US008123841B2

(12) United States Patent
Masel et al.

(10) Patent No.: US 8,123,841 B2
(45) Date of Patent: Feb. 28, 2012

(54) COLUMN DESIGN FOR MICRO GAS CHROMATOGRAPH

(75) Inventors: Richard I Masel, Champaign, IL (US); Mark Shannon, Champaign, IL (US); Adarsh D Radadia, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 454 days.

(21) Appl. No.: 12/337,856

(22) Filed: Dec. 18, 2008

(65) Prior Publication Data
US 2009/0178563 A1 Jul. 16, 2009

Related U.S. Application Data

(60) Provisional application No. 61/021,588, filed on Jan. 16, 2008, provisional application No. 61/021,620, filed on Jan. 16, 2008.

(51) Int. Cl.
*B01D 53/02* (2006.01)
(52) U.S. Cl. ............................ 96/101; 73/23.39; 73/23.42
(58) Field of Classification Search .................... 96/101; 73/23.35, 23.39, 23.42
See application file for complete search history.

(56) References Cited

U.S. PATENT DOCUMENTS

| | | | |
|---|---|---|---|
| 2,901,623 A | 8/1959 | Wouters | |
| 3,149,941 A * | 9/1964 | Barnitz et al. | ................. 96/101 |
| 3,168,823 A | 2/1965 | Reinecke et al. | |
| 3,345,858 A | 10/1967 | Fenske | |
| 3,357,232 A | 12/1967 | Lauer | |
| 3,461,519 A | 8/1969 | Raschle | |
| 3,538,744 A * | 11/1970 | Karasek | ...................... 73/23.39 |
| 3,568,411 A | 3/1971 | Dravnicks et al. | |
| 3,585,863 A | 6/1971 | Hrdina | |
| 3,675,466 A | 7/1972 | Linenberg | |
| 3,733,908 A | 5/1973 | Linenberg | |
| 3,769,837 A | 11/1973 | Kraus | |
| 3,797,318 A | 3/1974 | Palm | |
| 3,807,217 A | 4/1974 | Wilkins et al. | |
| 3,897,679 A | 8/1975 | Guild | |
| 3,923,461 A | 12/1975 | Barden | |
| 3,925,022 A | 12/1975 | Showalter et al. | |
| 3,950,980 A | 4/1976 | Braun et al. | |
| 3,985,017 A | 10/1976 | Goldsmith | |
| 4,040,085 A | 8/1977 | Jouanny | |
| 4,040,805 A | 8/1977 | Nelms et al. | |
| 4,084,440 A | 4/1978 | Carpenter et al. | |
| 4,128,008 A | 12/1978 | Linenberg | |

(Continued)

OTHER PUBLICATIONS

International Search Report, International Preliminary Report on Patentability and the Written Opinion, corresponding to the PCT application PCT/US06/29296 filed Jul. 26, 2006.

(Continued)

*Primary Examiner* — Robert Clemente
(74) *Attorney, Agent, or Firm* — Kilpatrick Townsend & Stockton LLP

(57) ABSTRACT

Improved micro-columns and methods for producing micro-columns particularly suitable for use in gas chromatographs are disclosed. In particular, following deposition of the stationary phase coating, the micro-columns are subjected to a postcoating treatment with a molecule that binds to the active sites in the stationary phase micro-column thereby eliminating or reducing loss of gas chromatograph performance associated with those active sites. The postcoating treatment molecule binds to the same active sites as the analytes of interest.

12 Claims, 22 Drawing Sheets

U.S. PATENT DOCUMENTS

| | | | |
|---|---|---|---|
| 4,129,424 A | 12/1978 | Armond | |
| 4,180,389 A | 12/1979 | Paul | |
| 4,235,097 A | 11/1980 | Kring et al. | |
| 4,293,316 A | 10/1981 | Block | |
| 4,293,415 A | 10/1981 | Bente et al. | |
| 4,301,114 A | 11/1981 | Rounbehler et al. | |
| 4,376,641 A | 3/1983 | Nestrick et al. | |
| 4,399,688 A | 8/1983 | Dennis | |
| 4,451,816 A | 5/1984 | Ball | |
| 4,498,850 A | 2/1985 | Perlov et al. | |
| 4,509,964 A | 4/1985 | Hubball et al. | |
| 4,541,268 A | 9/1985 | Odernheimer | |
| 4,585,209 A | 4/1986 | Aine et al. | |
| 4,599,095 A | 7/1986 | Barnes et al. | |
| 4,628,576 A | 12/1986 | Giachino et al. | |
| 4,647,013 A | 3/1987 | Giachino et al. | |
| 4,698,071 A | 10/1987 | Elias | |
| 4,701,306 A | 10/1987 | Lawrence et al. | |
| 4,713,091 A | 12/1987 | Govind | |
| 4,735,691 A | 4/1988 | Green et al. | |
| 4,759,210 A | 7/1988 | Wohltjen | |
| 4,778,666 A | 10/1988 | Chu et al. | |
| 4,805,441 A | 2/1989 | Sides et al. | |
| 4,819,477 A | 4/1989 | Fisher et al. | |
| 4,821,999 A | 4/1989 | Ohtaka | |
| 4,826,131 A | 5/1989 | Mikkor | |
| 4,865,746 A | 9/1989 | Overfield | |
| 4,885,830 A | 12/1989 | Ohtaka | |
| 4,895,500 A | 1/1990 | Hok | |
| 4,915,051 A | 4/1990 | Martinek | |
| 4,915,843 A | 4/1990 | Taniguchi et al. | |
| 4,977,095 A | 12/1990 | Zaromb | |
| 4,997,676 A | 3/1991 | Lefebvre | |
| 5,014,541 A | 5/1991 | Sides et al. | |
| 5,055,346 A | 10/1991 | Rohrbacher | |
| 5,069,419 A | 12/1991 | Jerman | |
| 5,082,242 A | 1/1992 | Bonne et al. | |
| 5,083,019 A | 1/1992 | Spangler | |
| 5,092,155 A | 3/1992 | Rounbehler et al. | |
| 5,092,217 A | 3/1992 | Achter et al. | |
| 5,092,218 A | 3/1992 | Fine et al. | |
| 5,110,551 A | 5/1992 | Michal | |
| 5,123,276 A | 6/1992 | Hartman et al. | |
| 5,142,143 A | 8/1992 | Fite et al. | |
| 5,162,652 A | 11/1992 | Cohen et al. | |
| 5,173,264 A | 12/1992 | Zaromb et al. | |
| 5,176,358 A | 1/1993 | Bonne et al. | |
| 5,180,623 A | 1/1993 | Ohnstein | |
| 5,216,273 A | 6/1993 | Doering et al. | |
| 5,224,972 A | 7/1993 | Frye et al. | |
| 5,288,310 A | 2/1994 | Peters et al. | |
| 5,294,418 A | 3/1994 | Ramprasad et al. | |
| 5,322,258 A | 6/1994 | Bosch et al. | |
| 5,323,999 A | 6/1994 | Bonne et al. | |
| 5,328,851 A | 7/1994 | Zaromb | |
| 5,395,589 A | 3/1995 | Nacson | |
| 5,417,235 A | 5/1995 | Wise et al. | |
| 5,441,597 A | 8/1995 | Bonne et al. | |
| 5,465,607 A | 11/1995 | Corrigan et al. | |
| 5,468,851 A | 11/1995 | Seeman et al. | |
| 5,481,110 A | 1/1996 | Krishnaswamy et al. | |
| 5,482,677 A | 1/1996 | Yao et al. | |
| 5,522,918 A | 6/1996 | Shiramizu | |
| 5,532,129 A | 7/1996 | Hellar | |
| 5,551,278 A | 9/1996 | Rounbehler et al. | |
| 5,585,575 A | 12/1996 | Corrigan et al. | |
| 5,589,396 A | 12/1996 | Frye et al. | |
| 5,619,177 A | 4/1997 | Johnson et al. | |
| 5,648,508 A | 7/1997 | Yaghi | |
| 5,720,798 A | 2/1998 | Nickerson et al. | |
| 5,753,832 A | 5/1998 | Bromberg et al. | |
| 5,763,360 A | 6/1998 | Gundel et al. | |
| 5,795,368 A | 8/1998 | Wright et al. | |
| 5,830,427 A | 11/1998 | Bedard et al. | |
| 5,836,750 A | 11/1998 | Cabuz | |
| 5,854,431 A | 12/1998 | Linker et al. | |
| 5,876,830 A | 3/1999 | Michl et al. | |
| 5,899,218 A | 5/1999 | Dugan | |
| 5,941,501 A | 8/1999 | Biegelsen et al. | |
| 5,970,804 A | 10/1999 | Robbat, Jr. | |
| 6,000,676 A | 12/1999 | Zengerle et al. | |
| 6,026,834 A | 2/2000 | Azima | |
| 6,085,601 A | 7/2000 | Linker et al. | |
| 6,098,661 A | 8/2000 | Yim et al. | |
| 6,110,247 A | 8/2000 | Birmingham et al. | |
| 6,126,140 A | 10/2000 | Johnson et al. | |
| 6,129,331 A | 10/2000 | Henning et al. | |
| 6,165,254 A | 12/2000 | Kawakami et al. | |
| 6,171,378 B1 | 1/2001 | Manginell et al. | |
| 6,182,941 B1 | 2/2001 | Scheurenbrand et al. | |
| 6,187,412 B1 | 2/2001 | Armacost et al. | |
| 6,215,221 B1 | 4/2001 | Cabuz et al. | |
| 6,223,584 B1 | 5/2001 | Mustacich et al. | |
| 6,251,260 B1 | 6/2001 | Heller et al. | |
| 6,345,545 B1 | 2/2002 | Linker et al. | |
| 6,355,793 B1 | 3/2002 | Lin | |
| 6,372,932 B1 | 4/2002 | Kepert et al. | |
| 6,384,253 B1 | 5/2002 | Khan | |
| 6,454,840 B1 * | 9/2002 | Gellert et al. | 96/101 |
| 6,455,003 B1 | 9/2002 | Anvia et al. | |
| 6,470,904 B1 | 10/2002 | Tai et al. | |
| 6,481,263 B1 | 11/2002 | Haley et al. | |
| 6,491,740 B1 | 12/2002 | Wang et al. | |
| 6,517,610 B1 | 2/2003 | de la Houssaye | |
| 6,523,393 B1 | 2/2003 | Linker et al. | |
| 6,527,835 B1 | 3/2003 | Manginell et al. | |
| 6,557,820 B2 | 5/2003 | Wetzel et al. | |
| 6,568,286 B1 | 5/2003 | Cabuz | |
| 6,604,406 B1 | 8/2003 | Linker et al. | |
| 6,607,580 B1 * | 8/2003 | Hastings et al. | 95/87 |
| 6,607,700 B1 | 8/2003 | Apte et al. | |
| 6,610,125 B2 | 8/2003 | Tripp et al. | |
| 6,626,416 B2 | 9/2003 | Sharma et al. | |
| 6,626,417 B2 | 9/2003 | Winger et al. | |
| 6,649,129 B1 | 11/2003 | Neal | |
| 6,656,738 B1 | 12/2003 | Vogel et al. | |
| 6,663,697 B1 | 12/2003 | Kottenstette et al. | |
| 6,666,907 B1 | 12/2003 | Manginell et al. | |
| 6,670,024 B1 * | 12/2003 | Yu | 428/209 |
| 6,685,841 B2 | 2/2004 | Lopez et al. | |
| 6,706,091 B1 | 3/2004 | Robinson et al. | |
| 6,719,828 B1 | 4/2004 | Lovell et al. | |
| 6,749,826 B2 | 6/2004 | Tillotson et al. | |
| 6,759,013 B2 * | 7/2004 | Kaltenbach et al. | 422/504 |
| 6,772,513 B1 | 8/2004 | Frye-Mason et al. | |
| 6,773,674 B2 | 8/2004 | Bannister et al. | |
| 6,783,680 B2 | 8/2004 | Malik | |
| 6,793,753 B2 | 9/2004 | Unger et al. | |
| 6,814,781 B2 | 11/2004 | Tonkovich et al. | |
| 6,830,229 B2 | 12/2004 | Wetzel et al. | |
| 6,834,671 B2 | 12/2004 | Cotte et al. | |
| 6,837,476 B2 | 1/2005 | Cabuz et al. | |
| 6,838,640 B2 | 1/2005 | Wise et al. | |
| 6,840,120 B2 | 1/2005 | Sakairi et al. | |
| 6,848,325 B2 | 2/2005 | Parmeter et al. | |
| 6,875,257 B2 | 4/2005 | Rodgers | |
| 6,893,564 B2 | 5/2005 | Mueller et al. | |
| 6,902,701 B1 | 6/2005 | Hughes et al. | |
| 6,910,394 B2 | 6/2005 | Kriel | |
| 6,913,697 B2 | 7/2005 | Lopez et al. | |
| 6,914,220 B2 | 7/2005 | Tian et al. | |
| 6,929,679 B2 | 8/2005 | Muller et al. | |
| 6,930,193 B2 | 8/2005 | Yaghi et al. | |
| RE38,797 E | 9/2005 | Linker et al. | |
| 6,965,026 B2 | 11/2005 | Zaworotko et al. | |
| 6,967,103 B2 | 11/2005 | Schwartz et al. | |
| 6,967,193 B1 | 11/2005 | Dang et al. | |
| 6,968,862 B2 | 11/2005 | Cabuz et al. | |
| 6,978,657 B1 | 12/2005 | Baumann et al. | |
| 6,984,524 B2 | 1/2006 | Nguyen et al. | |
| 6,986,365 B2 | 1/2006 | Henning et al. | |
| 6,986,500 B2 | 1/2006 | Giousouf et al. | |
| 6,989,044 B2 | 1/2006 | Zhang et al. | |
| 6,998,040 B2 | 2/2006 | Malik et al. | |
| 7,000,452 B2 | 2/2006 | Bonne et al. | |
| 7,008,193 B2 | 3/2006 | Najafi et al. | |
| 7,014,165 B2 | 3/2006 | Ji et al. | |

| | | | |
|---|---|---|---|
| 7,052,677 B1 | 5/2006 | Raptis et al. | |
| 7,147,695 B2 | 12/2006 | Mitra | |
| 7,654,129 B2 | 2/2010 | Bonne et al. | |
| 7,695,681 B2 | 4/2010 | Wang et al. | |
| 2002/0175302 A1 | 11/2002 | Wetzel | |
| 2003/0004364 A1 | 1/2003 | Yaghi et al. | |
| 2003/0078311 A1 | 4/2003 | Muller et al. | |
| 2003/0146401 A1 | 8/2003 | Wetzel | |
| 2003/0148165 A1 | 8/2003 | Muller et al. | |
| 2003/0222023 A1 | 12/2003 | Mueller et al. | |
| 2003/0231967 A1 | 12/2003 | Najafi et al. | |
| 2003/0234376 A1 | 12/2003 | Cabuz et al. | |
| 2004/0097724 A1 | 5/2004 | Muller et al. | |
| 2004/0137300 A1 | 7/2004 | Gemmen et al. | |
| 2004/0191125 A1 | 9/2004 | Kellogg et al. | |
| 2004/0225134 A1 | 11/2004 | Yaghi et al. | |
| 2004/0249189 A1 | 12/2004 | Mueller et al. | |
| 2004/0265670 A1 | 12/2004 | Muller et al. | |
| 2005/0004404 A1 | 1/2005 | Muller et al. | |
| 2005/0067029 A1 | 3/2005 | Henning | |
| 2005/0098435 A1 | 5/2005 | Jacobson et al. | |
| 2005/0101027 A1 | 5/2005 | Haas | |
| 2005/0124819 A1 | 6/2005 | Yaghi et al. | |
| 2005/0154222 A1 | 7/2005 | Muller et al. | |
| 2005/0164870 A1 | 7/2005 | Shan et al. | |
| 2005/0192175 A1 | 9/2005 | Yaghi et al. | |
| 2006/0037477 A1 | 2/2006 | Lopez et al. | |
| 2006/0049101 A1 | 3/2006 | Suib et al. | |
| 2006/0057057 A1 | 3/2006 | Muller et al. | |
| 2006/0071192 A1 | 4/2006 | Ohmi et al. | |
| 2006/0099398 A1 | 5/2006 | Hesse et al. | |
| 2006/0113231 A1 | 6/2006 | Malik | |
| 2006/0144237 A1* | 7/2006 | Liang et al. | 96/101 |
| 2006/0175238 A1 | 8/2006 | Lautamo | |
| 2006/0200044 A1 | 9/2006 | Freeman et al. | |
| 2006/0252641 A1 | 11/2006 | Yaghi et al. | |
| 2007/0023719 A1 | 2/2007 | Masel et al. | |
| 2007/0074717 A1 | 4/2007 | Law et al. | |
| 2007/0172960 A1 | 7/2007 | Malik et al. | |
| 2008/0149869 A1 | 6/2008 | Shannon et al. | |
| 2009/0131643 A1 | 5/2009 | Zheng et al. | |
| 2009/0178563 A1 | 7/2009 | Masel et al. | |
| 2009/0211452 A1 | 8/2009 | Masel et al. | |
| 2010/0075123 A1 | 3/2010 | Masel et al. | |
| 2010/0132547 A1 | 6/2010 | Masel et al. | |

OTHER PUBLICATIONS

International Preliminary Report on Patentability and Written Opinion corresponding to the PCT application PCT/US06/38998 filed Oct. 6, 2006.
International Search Report and Written Opinion corresponding to the PCT application PCT/US07/009243 filed Apr. 13, 2007.
International Preliminary Report and Written Opinion corresponding to the PCT application PCT/US2008/053959 filed Feb. 14, 2008.
Panda, A. B. et al., Microwave Synthesis of Highly Aligned Ultra Narrow Semiconductor Rods and Wires, J. Am. Chem. Soc., 128:2790-2791 (2006).
Tompsett, G. A. et al., Microwave Synthesis of Nanoporous Materials, ChemPhysChem, 7:296-319 (2006).
Lu, Q. et al., Biomolecule and/or Microwave-Assisted Solvothermal Syntheses of Nanomaterials, AZo Journal of Materials Online vol. 1, (2005).
Grudpan, K. et al., Flow injection spectrophotometric determination of As(III) and As(V) using molybdate reagent with solid phase extraction in-valve column, Indian Journal of Chemistry, 42A:2939-2944 (2003).
Luis Castaner et al., Speed-energy optimization of electrostatic actuators based on Pull-in, IEEE Journal of Microelectromechanical Systems, vol. 8, No. 3, pp. 257-265 (1999).
Han et al., Micro-fabricated membrane gas valves with a non-stiction coating deposited by $C_4F_8$/Ar plasma, J. Micromech. Microeng. 18 (2008) 095015, pp. 1-9.
Yeom et al., The design, fabrication and characterization of a silicon microheater for an integrated MEMS gas preconcentrator, J. Micromech. Microeng. 18 (2008) 125001, pp. 1-12.

Han et al. Surface energy approach and AFM verification of the (CF)n treated surface effect and its correlation with adhesion reduction in microvalves, J. Micromech. Microeng. 19 (2009) 085017, pp. 1-9.
Radadia et al., The fabrication of all-silicon micro gas chromatography columns using gold diffusion eutectic bonding, J. Micromech. Microeng. 20 (2010) 015002, pp. 1-7.
Radadia et al., Micromachined GC Columns for Fast Separation of Organophosphonate and Organosulfur Compounds, Anal. Chem. 2008, 80, pp. 4087-4094.
Radadia et al., Partially Buried Microcolumns for Micro Gas Analyzers, Anal. Chem. 2009, 81, pp. 3471-3477.
Han et al., Smooth Contact Capacitive Pressure Sensors in Touch- and Peeling-Mode Operation, IEEE Sensors Journal, vol. 9, No. 3, Mar. 2009, pp. 199-206.
Radadia et al., The Effect of Microcolumn Geometry on the Performance of Micro-Gas Chromatography Columns for Chip Scale Gas Analyzers, Sensors and Actuators B: Chemical (2010), doi:10.1016/j.snb.2010.07.002, pp. 1-29.
Bae et al., A Bidirectional Electrostatic Microvalve With Microsecond Switching Performance, Journal of Microelectromechanical Systems, vol. 16, No. 6, Dec. 2007, pp. 1461-1471.
Zhong et al., Characterization of a high-performance portable GC with a chemiresistor array detector, Analyst, 2009, 134, pp. 283-293.
Groves et al., Analyzing organic vapors in exhaled breath using a surface acoustic wave sensor array with preconcentration: Selection and characterization of the preconcentrator adsorbent, Analytica Chimica Acta 371 (1998) pp. 131-143.
Zheng Ni, et al., "Rapid Production of Metal-Organic Frameworks via Microwave-Assisted Solvothermal Synthesis," J. Am. Chem. Soc., (2006).
Jay W. Grate, et al., "Progressive Thermal Desorption of Vapor Mixtures from a Preconcentrator with a Porous Metal Foam Internal Architecture and Variable Thermal Ramp Rates," pp. 1867-1875, (2005).
R. W. Jotham, et al., "Anti ferromagnetism in transition-metal complexes. Part IV. Low-lying excited states of binuclear copper (II) carboxylate complexes," J. C. S. Dalton, pp. 428-438, (1972).
K. Tamada, et al., "The steady two-dimensional flow of viscous fluid at low Reynolds numbers passing through an infinite row of equal parallel circular cylinders," Quart. J. Mech. Appl. Math., 10, 1957, 425-432.
H. Hasimoto, "On the periodic fundamental solutions of the Stokes equations and their application to viscous flow past a cubic array of spheres," J. Fluid Mech., 5, 1959, pp. 317-328.
Michinobu Kato, et al., "Copper (II) complexes with subnormal magnetic moments," Richard Chemistry Lab, Tulane University, New Orleans Louisiana, Dec. 20, 1963 pp. 99-128.
Joseph B. Keller, "Viscous flow through a grating or lattice of cylinders," J. Fluid Mech. 18, 1964, 94-96.
Wolfgang Micklitz, et al., Heptadecanuclear mixed metal iron oxo-hydroxo complexes, $[Fe_{16}MO_{10}(OH)_{10}(O_2CPh)_{20}]$ M = Mn or Co, structurally comprised of two fragments derived from $[Fe_{11}O_6(OH)_6(O_2CPh)_{15}]$ Journal American Chemical Society (1989) vol. 111, pp. 6856-6858.
Bernard F. Hoskins, et al,, "Infinite polymeric frameworks consisting of three dimensionally linked rod-like segments," Journal of the American Chemical Society, vol. 111 No. 15, (1989) pp. 5962-5964.
Sergiu M. Gorun, et al., "Magnetostructural correlations in magnetically coupled (μ-Oxo)diiron(III) complexes," Inorganic Chemistry, 1991, 30(7) pp. 1625-1630.
Vinod S. Nair, et al., "Iron Oxo aggregation: $Fe_3$ to $Fe_6$. Synthesis, structure, and magnetic properties of the hexanuclear dication $[Fe_6(\mu_4\text{-}O)_2(\mu_2\text{-}OMe)_8(OMe)_4(tren)_2]^{2+}$, a soluble, crystalline model of iron Oxo hydroxo nanoparticles, the core of ferritin and rust formation," Inorganic Chemistry (1992) vol. 31, pp. 4048-4050.
Steven C. Shoner, et al., "Neutral catecholate derivatives of manganese and iron: Synthesis and characterization of the metal-oxygen cubane-like species $M_4(DBCat)_4(py)_6$ (M = Mn, Fe), the trinuclear complex $Mn_3(DBCat)_4(py)_4$ and the dimers $M_2(DBCat)_2(py)_n$ (M = Mn, n = 6; M = Fe, n = 4,6)," Inorganic Chemistry (1992), 31, pp. 1001-1010.

C.T. Kresge, et al., "Ordered mesoporous molecular sieves synthesized by a liquid-crystal template mechanism," Nature, vol. 359, Oct. 22, 1992, pp. 710-712.

Kingsley L. Taft, et al., "Iron and manganese alkoxide cubes," Journal of American Chemical Society, (1993) vol. 115, pp. 11753-11766.

Andreas Stein, et al., "Turning down the heat: design and mechanism in solid-state synthesis," Science, vol, 259, No. 5101, Mar. 12, 1993, pp. 1558-1564.

Alan Wilson, et al., "Detection of Nitro Compounds by Organic Semiconductor Sensors," Sensors and Actuators B 18-19, 1994, pp. 511-514.

Kingsley L. Taft, et al., "Synthesis, structure, and electronic properties of a mixed-valent dodecairon Oxo complex, a model for the biomineralization of ferritin," Inorganic Chemistry, (1994) 33, pp. 1510-1520.

B.F. Abrahams, et al., "Assembly of porphyrin building blocks into network structures with large channels," Nature vol. 369, Jun. 30, 1994 pp. 727-729.

O.M. Yaghi, et al., "Hydrothermal Synthesis of a Metal-Organic Framework Containing Large Rectangular Channels," J. Am. Chem. Soc. 1995, 117, 10401-10402.

Katerina Dimitrou, et al., "The $[CO_4O_4]^{4+}$ cubane as a quadruply-bridging unit: the mixed-valence cluster $[Co_8O_4(O_2CPh)_{12}solv_4]$ solv = DMF, MeCN, $H_2O$)," Inorganic Chemistry, 1995, 34, pp. 4160-4166.

O. M. Yaghi, et al., "Hydrothermal synthesis of a metal-organic framework containing large rectangular channels," Journal of the American Chemical Society, 1995, vol. 117, pp. 10401-10402.

O.M. Yaghi, et al., "Selective Binding and Removal of Guests in a Microporous Metal-Organic Framework," Nature, Dec. 14, 1995, vol. 378, pp. 703-706.

O.M. Yaghi, et al., "T-Shaped Molecular Building Units in the Porous Structure of Ag(4,4'-bpy)•$NO_3$," J. Am. Chem. Soc. 1996, 118, pp. 295-296.

O. M. Yaghi, et al., "Construction of porous solids from hydrogen-bonded metal complexes of 1,3,5-benzenetricarboxylic acid," Journal of the American Chemical Society, (1996), vol. 118, pp. 9096-9101.

William A. Groves, et al., "Prototype Instrument Employing a Microsensor Array for the Analysis of Organic Vapors in Exhaled Breath," American Industrial Hygiene Association Journal 57:1103-1108, Dec. 1996.

Scott Hynek, et al., "Hydrogen storage by carbon sorption," Int. J. Hydrogen Energy vol. 22, No. 6, pp. 601-610 (1997).

Jian Lu, et al., "Coordination Polymers of Co(NCS)$_2$ with Pyrazine and 4,4'-Bipyridine: Syntheses and Stuctures," Inorganic Chemist (1997) vol. 36, pp. 923-929.

Christoph Janiak, "Functional organic analogues of zeolites bases on metal-organic coordination frameworks," Angew. Chem. Int. Ed. Engl. (1997) 36, No. 13/14 pp. 1431-1434.

Mario V. Capparelli, et al., "X-ray crystallographic structure of $Ga_8(pz)_{12}O_4Cl_4$•2thf: a novel gallium pyrazololate complex with a $Ga_4O_4$ core," Chem. Comm., (1997) pp. 937-938.

O. M. Yaghi, et al., "Crystal growth of extended solids by nonaqueous gel diffusion," Chemical Materials, (1997) vol. 9, pp. 1074-1076.

Omar M. Yaghi, et al., "Construction of a new open-framework solid from 1,3,5-cyclohexane-tricarboxylate and zinc(II) building blocks," Journal Chem. Soc. Dalton Trans., (1997), pp. 2383-2384.

Victoria A. Russell, et al., "Nanoporous molecular sandwiches: pillared two-dimensional hydrogen-bonded networks with adjustable porosity," Science, vol. 276, Apr. 25, 1997, pp. 575-579.

Helmut Beinert, et al., "Iron-sulfur clusters: Nature's modular, multipurpose structures," Science, vol. 277, Aug. 1997, pp. 653-659.

Omar M. Yaghi, et al., "Synthetic Strategies, Structure Patterns, and Emerging properties in the chemistry of modular porous solids," Accounts of Chemical Research, vol. 31, No. 8, 1998, pp. 474-484.

William A. Groves, et al., "Analyzing organic vapors in exhaled breath using a surface acoustic wave sensor array with preconcentration: Selection and characterization of the preconcentrator adsorbent," Analytica Chimica Acta 371, 1998, pp. 131-143.

Michael W. Willer, et al., "Ligand Substitution Reactions of $[Re_6S_8Br_6]^{4-}$: A Basis Set of $Re_6S_8$ Clusters for Building Multicluster Assemblies," Inorganic Chemistry, (1998) vol. 37, pp. 328-333.

Hailian Li, et al., "Coordinatively unsaturated metal centers in the extended porous framework of $Zn_3(BDC)_3$•$6CH_3OH$ (BDC = 1,4-benzenedicarboxylate)," Journal of American Chemical Society, 1998, vol. 120, pp. 2186-2187.

Stuart L. James, et al., "Anion-templated formation of a unique inorganic 'super adamantoid' cage $[Ag_6(triphos)_4(O_3SCF_3)_4]^{2+}$ [triphos = $(PPh_2CH_2)_3CMe$]," Chemical Communication (1998) pp. 2323-2324.

M. John Plater, et al., "Hydrothermal synthesis and characterization of M(pdc)•$3H_2O$ (pdc = 2,5-pyridinedicarboxylate); M=Co, Ni, $Co_xNi_y$ (x = 0.4-0.6, y=0.6-0.4)," Journal of Chemical Research, (1998), pp. 3356-3376.

Cameron J. Kepert, et al., "A porous chiral framework of coordinated 1,3,5-benzenetricarboxylate: quadruple interpenetration of the (10,3)-a network," Chem Communication (1998) pp. 31-32.

Christopher W. Jones, et al., "Organic-functionalized molecular sieves as shape-selective catalysts," Nature vol. 393, May 7, 1998, . 52-54.

Lin, et al., "A Novel Ocupolar Metal-Organic NLO Material Based on a Chiral 2D Coordination Network," J. Am Chem. Soc. 1999, 121, 11249-11250.

Chui, et al., "A Chemically Functionalizable Nanoporous Material $[Cu_3(TMA)_2(H_2O)_3]n$," Science, 1999, vol. 283, pp. 1148-1150.

Jack Y. Lu, et al., "A new type of Two-Dimensional Metal Coordination Systems: Hydrothermal Synthesis and Properties of the First Oxalate-bpy Mixed-Ligand Framework $^2[(M (ox)(bpy)]$ (M=Fe(II), CO(II), Ni(II), Zn(II); ox = $C_2O_4^{2-}$; bpy = 4,4'-bipyridine)," Inorganic Chem. 1999, 38, pp. 2695-2704.

Srinivasan Natarajan, et al., "Layered Tin (II) Oxalates possessing large apertures," Chemical Material, 1999, 11 pp. 1633-1639.

Mitsuru Kondo, et al., "Rational synthesis of stable channel-like cavities with methane gas adsorption properties: $[\{Cu_2(pzdc)_2(L)\}_n]$ (pzdc = pyrazine-2,3-dicarboxylate; L = a pillar ligand)," Angew. Chem. Int. Ed. (1999) 38, No. ½, pp. 140-143.

Raphael G. Paptis, et al., "A $Fe^{III}$/Oxo cubane contained in an octanuclear complex of T symmetry that is stable over., five oxidation states," Angew, Chem. Int. Ed. (1999), vol. 38, No. 11, pp. 1632-1634.

Mohamed Eddaoudi, et al., "Design and synthesis of metal-carboxylate frameworks with permanent microporosity," Topics in Catalysis, 1999, vol. 9, pp. 105-111.

Stephen S.-Y Chui, et al., "A chemically functionalizable nanoporous material $[Cu_3(TMA)_2(H_2O)_3]_n$," Science, vol. 283, Feb. 19, 1999, pp. 1148-1150.

Hailian Li, et al., "Design and synthesis of an exceptionally stable and highly porous metal-organic framework," Nature, vol. 402, Nov, 18, 1999, pp. 276-279.

Seo, et al., "A Homochiral Metal-organic Porous Material for Enantioselective Separation and Catalysis," Nature, 2000, 404, pp. 982-986.

Jeongim Park, et al., "Temperature and Humidity Compensation in the Determination of Solvent Vapors with a Microsensor System," The Royal Society of Chemistry, Analyst, 2000, 125, pp. 1775-1782.

Edward T. Zellers, et al., "Evaluating Porous-Layer Open-Tubular Capillaries as Vapor Preconcentrators in a Microanalytical System," Sensors and Actuators B 67, 2000, pp. 244-253.

Qing-Yun Cai, et al., "Vapor Recognition with an Integrated Array of Polymer-Coated Flexural Plate Wave Sensors," Sensors and Actuators B 62, 2000, pp. 121-130.

M.O. O'Keeffe, et al., "Frameworks for extended solids: geometrical design principles," Journal of Solid State Chemistry 152, pp. 3-20, 2000.

Shouheng Sun, et al., "Monodisperse FePt nanoparticles and ferromagnetic FePt nanocrystals superlattices," Science. vol. 287, Mar. 17, 2000, pp. 1989-1992.

Xi Xiang Zhang, et al., "Cooperative magnetic behavior in the coordination polymers $[Cu_3(TMA)_2L_3]$ (L=$H_2O$, pyridine)," Journal of Applied Physics, vol. 87, No. 9 May 1, 2000, pp. 6007-6009.

R. Murugavel, et al., "Extended metal-organic solids based on benzenepolycarboxylic and aminobenzoic acids," Proc. Indian Acad. Sci. (Chem. Sci.) vol. 112, No. 3, Jun. 2000, pp. 273-290.

Jaheon Kim, et al., "Assembly of Metal-Organic Frameworks from Large Organic and Inorganic Secondary Building Units: New Examples and Simplifying Principles for Complex Structures," J. Am. Chem. Soc. 2001, 123, pp. 8239-8247.

Banglin Chen, et al., "Interwoven Metal-Organic Framework on a Periodic Minimal Surface with Extra-Large Pores," Science, Feb. 9, 2001, vol. 291, pp. 1021-1023.

Usan A. Bourne, et al., "Coexisting Covalent and Noncovalent Nets: Parallel Interpenetration of a Puckered Rectangular Coordination Polymer and Aromatic Noncovalent Nets," Chem. Comm., 2001, pp. 861-862.

Chang-Ge Zheng, et al., "A novel two-dimensional layer network composed of cadmium and bridging isophthalate ligand," Inorganic Chemistry Communications 4, (2001), pp. 165-167.

Brian Moulton, et al., "From molecules to crystal engineering: supramolecular isomerism and polymorphism in network solids," Chemical Reviews, 2001, vol. 101 No. 6, pp. 1629-1658.

Cynthia Stowell, et al., "Self-Assembled honeycomb networks of gold nanocrystals," Nanoletters, (2001) vol. 1, No. 11, pp. 595-600.

Yucang Liang, et al., "Hydrothermal synthesis and characterization of the coordination polymer $[Zn(bbdc)(H_2O)]_n$ (bbdc = 4,4'-bibenzene-dicarboxylate) possessing a 3D network structure," Inorganic Chemistry Communications 4 (2001) pp. 599-601.

Yen-Hsiang Liu, et al., "Hydrothermal synthesis, crystal structure, and magnetic property of copper (II) coordination networks with chessboard tunnels," Journal of Solid State Chemist 158 2001 vol. 158, pp. 315-319.

Chuan-De Wu, et al., "Hydrothermal synthesis of two new zinc coordination polymers with mixed ligands," Inorganic Chemistry Communications 4 (2001) pp. 561-564.

H. Tamura, et al., "Semiconductor ferromagnetism in quantum dot array," Physical Stat. Sol. (b) 224, No. 3, (2001), pp. 723-725.

Ashleigh J. Fletcher, et al., "Adsorption dynamics of gases and vapors on the nanoporous metal organic framework material $Ni_2(4,4'$-bipyridine$)_3(NO_3)_4$: Guest modification of host sorption behavior," Journal of the American Chemical Society (2001), vol. 123, pp. 10001-10011.

Kumar Biradha, et al., "2D and 1D coordination polymers with the ability for inclusion of guest molecules: nitrobenzene, benzene, alkoxysilanes," Journal of Inclusion Phenomena and Macrocyclic Chemistry 49, (2001) pp. 201-208.

Mohamed Eddaoudi, et al., "Modular Chemistry: Secondary building units as a basis for the design of highly porous and robust metal-organic carboxylate frameworks," Acc. Chem. Res. 2001, vol. 34, pp. 319-330.

Jaheon Kim, et al., "Assembly of metal-organic frameworks from large organic and inorganic secondary building units:. new examples and simplifying principles for complex stntctures," Journal of the American Chemical Society, (2001), vol. 123, pp. 8239-8247.

Susan A. Bourne, et al., "Self-assembly of nanometer-scale secondary building units into an undulating two-dimensional network with two types of hydrophobic cavity," Angew. Chem. Int. Ed., (2001), vol. 40, No. 11, pp. 2111-2113.

Jianjiang Lu, et al., "Polygons and faceted polyhedra and nanoporous networks," Angew. Chem. Int. Ed., (2001), vol. 40, No. 11, pp. 2113-2116.

Brian Moulton, et al., "Nanoballs: nanoscale faceted polyhedra with large windows and cavities," Chem. Commun., (2001), pp. 863-864.

Heba Abourahma, et al., "Hydroxylated nanoballs: synthesis, crystal structure, solubility and crystallization on surfaces," Chem. Comm., (2001), pp. 2380-2381.

Susan A. Bourne, et al., "1-D coordination polymers containing benzenedicarboxylate," Crystal Engineering, (2001), vol. 4, pp. 25-36.

Chia-Jung Lu, et al., "A Dual-Adsorbent Preconcentrator for a Portable Indoor-VOC Microsensor System," Analytical Chemistry, vol. 73, No. 14, Jul. 15, 2001, pp. 3349-3457.

Kosal, M.E., et al., "A functional zeolite analogue assembled from metalloporphyrins," Nature Materials, 2002, vol. 1, pp. 118-121.

Xingling Xu, et al., "A nanoporous metal-organic framework based on bulky phosphane ligands," Angew. Chem. Int. Ed, (2002) 41, No. 5 pp. 764-767.

Filipe A. Almeida Paz, et al., "Synthesis and characterization of a novel modular cadmiurn-organic framework with biphenyl-4,4'-dicarboxylate," Eur. J. Inorg, Chem. (2002) pp. 2823-2828.

Zi-Guang Sun, et al., "Guest controlled coordination framework: syntheses, crystal structures and thermal properties of two three-dimensional structures of $[Ce_2(adipate)_3(OH_2)_4]$• $6H_2O$ and $[Ce_2(adipate)_3(OH_2)_4]$• $4H_2O$ • (adipic acid)," Inorganic Chemist Communications 5 (2002) pp. 629-632.

Ljiubov Morris, et al., "Simple system for part-per-billion-level volatile organic compound analysis in groundwater and urban air," Measurement Science and Technology, 13, (2002) pp. 603-612.

Ming Wen, et al., "Porous silver (I) organometallic coordination polymer of triptycene, and the guest desorption and absorption," Inorganica Chimica Acta 340 (2002) pp. 8-14.

Edmund J. Cussen, et al., "Flexible sorption and transformation behavior in a microporous metal-organic framework," Journal of the American Chemical Society (2002), vol. 124, pp. 9574-9581.

Yu-Cang Liang, et al., "Hydrothermal syntheses, structural characterizations and magnetic properties of cobalt (II) and manganese(II) coordination polymeric complexes containing pyrazinecarboxylate ligand," Inorganica Chimica Acta 328, (2002), pp. 152-158.

Jun Tao, et al., "Assembly of a microporous metal-organic framework [Zn(bpdc)(DMSO)] (bpdc = 4,4-biphenyldicarboxylate) based on paddle-wheel units affording guest inclusion," Inorganic Chemistry Communications, (2002), vol. 5, pp. 975-977.

Mohamed Eddaoudi, et al., "Systematic Design of Pore Size and Functionality in Isoreticular MOFs and Their Application in Methane Storage," Science, Jan. 18, 2002, vol. 295, pp. 469-472.

Yaghi, et al., "Reticular Synthesis and the Design of New Materials," Nature 423, 2003, pp. 705-714.

Smithenry, D.W., et al., "A Robust Microporous Zinc Porphyrin Framework Solid," Inorg. Chem. 2003, vol. 42, pp. 7719-7721.

Jinxi Chen, et al., "A new open metal-organic framework $[(Zn_8(GeO_4)(C_8H_4O_4)_6)_n$, Constucted by Heterometallic Cluster $Zn_8(GeO_4)$ Secondary Building Units," Chemist Letters vol. 32, No. 5 (2003).

Enrique Colacio, et al., "Hydrothermal syntheses, crystal structures, and properties of two-dimensional homo- and heterometallic cyanide-bridged complexes: $[CU_2(CN)_2(bpym)]$ and $[Fe((bipy)_2(CN)_4CU_2]$ [(bpym = 2,2'—Bipyrimidine, bipy = 2,2'-Bipyridine)," Inorganic Chemist 2003, 42, pp. 4209-4214.

Li-Ping Zhang, et al., "Hydrothermal synthesis and crystal structures of three novel lanthanide coordination polymers with glutarate and 1,10 phenanthroline," Journal of Molecular Structure 646 (2003) pp. 169-178.

Li-Ping Zhang, et al., "Hydrothermal synthesis and crystal structure of neodymium(III) coordination polymers with isophthalic acid and 1,10-phenanthroline," Polyhedron 22 (2003) pp. 981-987.

Hidekazu Arii, et al., "Unique three-dimensionally expanded nanoporous structure constructed with a Cu(I) and cis, cis-1,3,5-triaminocyclohexane having a 3-fold axial symmetry," Chemist Letters vol. 32 No. 1 (2003) pp. 106-107.

Aleksey Vishnyakov, et al., "Nanopore structure and sorption properties of Cu-BTC metal-organic framework," Nano Letters, vol. 3, No. 6, (2003) pp. 713-718.

T. J. Prior, et al., "Designed layer assembly: a three-dimensional framework with 74% extra-framework volume by connection of infinite two-dimensional sheets," Chem. Commun., (2003), pp. 500-501.

Yang-Guang Li, et al., A novel three-dimensional metal-organic framework constructed from two-dimensional interpenetrating layers based on trinuclear cobalt clusters: $[Co_3(btec)(C_2O_4)(H_2O_2]_n$. Eur. Journal of Inorganic Chemistry (2003) pp. 2567-2571.

Sujit K. Ghosh, et al., "Coexistence of water dimer and hexamer clusters in 3D metal-organic framework structures of Ce(III) and Pr(III) with pyridine-2 6-dicarboxylic acid," Inorganic Chemistry, (2003) vol. 42, pp. 8250-8254.

Hee K. Chae, et al., "Design of frameworks with mixed triangular and octahedral building blocks exemplified by the structure of $[Zn_4O(TCA)_2]$ having the pyrite topology," Angew. Chem. Int. Ed., (2003), vol. 42, pp. 3907-3909.

Nathaniel L. Rosi, et al., "Hydrogen Storage in Microporous Metal-Organic Frameworks," Science, May 16, 2003, vol. 300, pp. 1127-1129.

Wei-Cheng Tian, et al., "Microfabricated Preconcentrator-Focuser for a Microscale Gas Chromatograph," Journal of Microelectromechanical Systems, vol. 12, No. 3, Jun. 2003, pp. 264-272.

Yun-Qi Tian, et al., "{[In$_3$ (pzdc)$_6$]$^{3-}$}{ Metal-Organic Framework of Distorted NbO-like Net (pzdc = Pyrazine-2,3-dicarboxylato)," Chemistry Letters vol. 32, No. 9, pp. 796-797, Aug. 4, 2003.

Jason K. Holt, et al., "Fabrication of a Carbon Nanotube-Embedded Silicon Nitride Membrane for Studies of Nanometer-Scale Mass Transport," American Chemical Society, Nano Letters 2004, vol. 4, No. 11, pp. 2245-2250.

Jessee L.C. Rowsell, et al., "Metal-organic frameworks: a new class of porous materials," Microporous and Mesoporous Materials 73, 2004, pp. 3-14.

Suman Mukhopadhyay, et al., "Honeycomb Nets with Interpenetrating Frameworks Involving Iminodiacetato-Copper (II) Blocks and Bipyridine Spacers: Syntheses, Characterization, and Magnetic Studies," Inorganic Chemistry, 2004, 43, pp. 3413-3420.

Mind-Hua Zeng, et al., "Crystal-to-crystal transformations of a microporous metal-organic laminated framework triggered by guest exchange, dehydration and readsorption," Dalton Trans., 2004, pp. 2217-2223.

Junji Ito, et al., "Discrimination of halitosis substance using QCM sensor array and a preconcentrator," Sensors and Actuators B 99 (2004) pp. 431-436.

Qiang Wei, et al., "A manganese metal-organic framework which remains crystalline on desolvation, and which gives insight into the rotational freedom of framework aromatic groups," Microporous and Mesoporous Materials 73 (2004) pp. 97-100.

Xiang-Jun Zheng, et al., "Hydrothermal syntheses, structures and magnetic properties of two transition metal coordination polymers with a square grid framework," Polyhedron 23, (2004) pp. 1257-1262.

Klaus Schlichte, et al., "Improved synthesis, thermal stability and catalytic properties of the metal-organic framework compound $Cu_3(BTC)_2$" Microporous and Mesoporous Materials 73 (2004) pp. 81-88.

Danil N. Dybtsev, et al., "Rigid and flexible: A Highly Porous Metal-Organic Framework with Unusual Guest-Dependent Dynamic Behavior," Angew. Chem. Int. Ed. (2004) 43, pp. 5033-5036.

Danil N Dybtsev, et al., "Three-dimensional metal-organic framework with (3,4)-connected net, synthesized from an ionic liquid medium," Chem. Commun. (2004) pp. 1594-1595.

Ryo Kitaura, et al., "Rational Design and Crystal Structure Determination of a 3-D Metal-Organic Jungle-Gym-Like Open Framework," Inorganic Chemist (2004), vol. 43, No. 21, pp. 6522-6524.

Filipe A. Almeida Paz, et al., "Synthesis and Characterization of a Novel Cadmium-Organic Framework with Trimesic Acid and 1,2-Bis(pyridl)ethane," Inorganic Chemistry (2004),vol. 43, No. 13, pp. 3948-3954.

Eithne Tynan, et al., "Solvent templated synthesis of metal-organic frameworks: structural characterization and properties of the 3D network isomers ([Mn(dcbp)] • ½ DMF}$_n$ and {[Mn(dcbp)] • 2H$_2$O)$_n$," Chem. Comm. (2004), pp. 776-777.

Haitao Xu, et al., "Two new microporous coordination polymers constructed by ladder-like and ribbon-like molecules with cavities," Journal of Molecular Structure 693 (2004) pp. 11-15.

Cheng-Yong Su, et al., "A three-dimensional, noninterpenetrating metal-organic framework with the moganite topology: a simple ($4^2$. $6^2.8^2$)($4.6^4.8$)$_n$ net containing two kinds of topologically nonequivalent points," Inorganic Chemistry Communication (2004), vol. 43, pp. 6881-6883.

Cheng-Yong Su, et al., "Exceptionally stable, hollow tubular metal-organic architectures: synthesis, characterization, and solid-state transformation study," Journal of the American Chemical Society, (2004) vol. 126, pp. 3576-3586.

Giannis S. Papaefstathiou, et al., "A 2D metal-organic framework with two different rhombus-shaped cavities: a rare example of a (4,4)-net with alternating metal and organic nodes," Microporous and Mesoporous Materials 71(2004) pp. 11-15.

Yan Bai, et al., "A three dimensional porous metal-organic framework [Fe$_4$L$_6$ • (DMF)$_3$ • (H$_2$O)$_{10}$] constructed from neutral discrete Fe$_4$L$_6$ pyramids [H$_2$L = 1,3-benzodihydroxamix acid]," Chem, Commun., (2004) pp. 186-187.

M. J. Rosseinsky, "Recent developments in metal-organic framework chemistry: design, discovery, permanent porosity and flexibility," Microporous and Mesoporous Materials 73(2004), pp. 15-30.

Hye Jin Choi, et al., "Dynamic and redox active pillared bilayer open framework: single-crystal-to-single crystal transformations upon guest removal, guest exchange, and framework oxidation," Journal of the American Chemical Society, (2004), vol. 126, pp. 15844-15851.

Ashleigh J. Fletcher, et al., "Adsorption of gases and vapors on nanoporous Ni$_2$(4,4'-bipyridine)$_3$(NO$_3$)$_4$ metal-organic framework materials templated with methanol and ethanol: structural effects in adsorption kinetics," Journal of the American Chemical Society, (2004), vol. 126, pp. 9750-9759.

Xinlong Wang, et al., "Designed double layer assembly: a three-dimensional open framework with two types of cavities by connection of infinite two-dimensional bilayer," Chem. Comm., (2004), pp. 378-379.

Yaqin Guo, et al., "Synthesis and Crystal Structure of a Novel Three-Dimensional Supramolecular Network Containing One-Dimensional Honeycomb-Like Channels," Inorganica Chimica Act vol. 357, (2004) pp. 4582-4586.

Liying Duan, et al., "Hydrothermal synthesis and crystal structures of two novel rare earth coordination polymers based on pyridine-2,6-dicarboxylic acid," Journal of Molecular Structure 689, (2004) pp. 269-274.

Sujit K. Ghosh, et al., "Puckered-boat conformation hexameric water clusters stabilized in a 2D metal-organic framework structure built from Cu(II) and 1,2,4,5-benzenetetracarboxylic acid," Inorganic Chemistry, (2004), vol. 43, pp. 5180-5182.

Hee K. Chae, et al., "A route to high surface area, porosity and inclusion of large molecules in crystals," Nature, vol. 427, Feb. 2004, pp. 523-527.

Xuebo Zhao, et al., "Hysteretic adsorption and desorption of hydrogen by nanoporous metal-organic frameworks," Science, vol. 306, Nov. 5, 2004, pp. 1012-1015.

Dat T. Tran, et al., "Open Metal-Organic Framework Containing Cuprate Chains," Inorganic Chemistry, vol. 44, No. 18, 2005, pp. 6192-6196.

Chia-Jung Lu, et al., "First-Generation Hybrid MEMS Gas Chromatograph," Lab on a Chip, 2005, 5, pp. 1123-1131.

C.E. Davis, et al., "Enhanced Detection of m-xylene Using a Preconcentrator with a Chemiresistor Sensor," Sensors and Actuators B 104, 2005, pp. 207-216.

A.T. Carvalho, et al., "Improvement on Organic Compound Adsorption and/or Detection by Using Metallic Thin Films Deposited onto Highly Rough Silicon Substrates," Sensors and Actuators B 108, 2005, pp. 947-954.

Yanjun Tang, et al., "A Micro-post Preconcentrator for a Microscale Gas Chromatography System," 2005 Micro Total Analysis Systems Conference (Boston, MA, Oct. 2005); Transducers Research Foundation Proceedings of the 2005 Micro Total Analysis Systems Conference, p. 660-662 (2005).

Bing-Bing Ding, et al., "Pillared-Layer Microporous Metal-Organic Frameworks Constructed by Robust Hydrogen Bonds. Synthesis, Characterization, and Magnetic and Adsorption Properties of 2,2'-Biimidazole and Carboxylate Complexes," Inorganic Chemist vol, 44, No. 224, 2005, pp. 8836-8845.

Qianrong Fang, et al., "A metal-organic framework with the ziolite MTN Topology containing large cages of volume 2.5 nm$^3$," Angew. Chem. Int. Ed. 2005, 44, pp. 3845-3848.

Banglin Chen, et al., "High H$_2$ adsorption in a microporous metal-organic framework with open metal sites," Angew. Chem. Int. Ed. 2005, 44, pp. 4745-4749.

Drew L, Murphy, et al., "A chiral, heterometallic metal-organic framework derived from a tris(chelate) coordination complex," Chemist Communication, 2005, pp. 5506-5508.

Radu Custelcea, et al., "A metal-organic framework functionalized with free carboxylic acid sites and its selective binding of a Cl(H$_2$O)$_4$-cluster," J. Am. Chem. Soc. 2005, 127, pp. 16362-16363.

Thomas Devic, et al., "MIL-103, A 3-D lanthanide-based metal organic framework with large one-dimensional tunnels and a high surface area," J. Am. Chem. Soc. 2005, 127, pp. 12788-12789.

Jarrod F. Eubank, et al,, "Terminal co-ligand directed synthesis of a neutral, non-interpenetrated (10,3)-α metal-organic framework," Chemical Communication, 2005, pp. 2095-2097.

Lei Wang, et al., "Two-dimensional metal-organic framework constructed from 4,4'-bipydine and 1,2,4-benzenetricarboxylate: synthesis, structure and magnetic properties," Journal of Solid State Chemistry, 178 (2005) pp. 3359-3365.

Ru-Qiang Zou, et al., "A hydrogen-bonded 3D coordination network of $Co^{II}$ with 4-(p-benzoxy)-1,2,4-triazole: hydrothermal synthesis, characterization, crystal structure and emission property," Journal of Molecular Structure 737 (2005) pp. 125-129.

Jun Hong, "[$Zn_2$ (BTDA)(bpy)($H_2$ O)]•0.5bpy: a new three-dimensional metal-organic framework constructed from flexible and rigid mixed ligands," Journal of Molecular Structure 752 (2005) pp. 166-169.

Henrik Fano Clausen, et al., "Solvothermal synthesis of new metal organic framework structures in the zinc-terephthalic acid-dimethyl formamide system" Journal of Solid State Chemist 178, (2005) pp. 3342-3351.

Giovanni Garberoglio, et al., "Adsorption of gases in metal organic materials: comparison of simulations and experiments," Journal of Physical Chemist B (2005) 109, pp. 13094-13103.

Gregory J. Halder, et al., "In situ single-crystal x-ray diffraction studies of desorption and sorption in a flexible nano porous molecular framework material," Journal of the American Chemical Society (2005), 127, pp. 7891-7900.

Ryo Kitaura, et al., "Formation and characterization of crystalline molecular arrays of gas molecules in a 1-dimensional ultramicropore of a porous copper coordination polymer," Journal of Physical Chemist B, (2005) 109, pp. 23378-23385.

Zheming Wang, et al., "Synthesis and characterization of a porous magnetic diamond framework, $Co_3(CHOO)_6$, and its $N_2$ sorption characteristic," Inorganic Chemist (2005), vol. 44, No. 5, pp. 1230-1237.

Hendrik Dathe, et al., "Metal organic frameworks based on $Cu^{2+}$ and benzene-1,3,5-tricarboxylate as host for $SO_2$ trapping agents," C. R. Chimie 8 (2005) pp. 753-763.

Jeong Yong Lee, et al., "Gas sorption properties of microporous metal organic frameworks," Journal of Solid State Chemist 178 (2005) pp. 2527-2532.

Jeong Yong Lee, et al., "Achieving high density of adsorbed hydrogen in microporous metal organic frameworks," Advanced Materials (2005) vol. 17, pp. 2703-2706.

Carine Livage, et al., "A three-dimensional metal-organic framework with an unprecedented octahedral building unit," Angew. Chem. Int. Ed. (2005) vol. 44, pp. 6488-6491.

Andrea M. Goforth, et al., "Connecting small ligands to generate large tubular metal-organic architectures," Journal of Solid State Chemist 178, pp. 2511-2518, (2005).

Linhua Xie, et al., "A three-dimensional porous metal-organic framework with the rutile topology contructed from triangular and distorted octahedral building blocks," Chem. Comm., (2005) pp. 2402-2404.

Giannis S. Papaefstathiou, et al,, "Design and construction of a 2D metal organic framework with multiple cavities: a nonregular net with a paracyclophane that codes for multiply fused nodes," Journal of the American Chemical Society, vol. 127, No. 41 (2005) pp. 14160-14161.

O. I. Lebedev, et al., "First direct imaging of giant pores of the metal-organic framework MIL-101," Chemistry Materials, (2005), vol. 17, pp. 6525-6527.

Dat T. Tran, et al., "Open metal-organic framework containing cuprate chains," Inorganic Chemistry, (2005) vol. 44, No. 18, pp. 6192-6196.

Ashleigh J. Fletcher, et al., "Flexibility in metal-organic framework materials: Impact on sorption properties," Journal of Solid State Chemist 178, (2005) pp. 2491-2510.

Tatsuhiko Sagara, et al., "New isoreticular metal-organic framework materials for high hydrogen storage capacityj," The Journal of Chemical Physics 123, 214707 (2005), pp. 1-6.

Tatsuhiko Sagara, et al., "Binding energies of hydrogen molecules to isoreticular metal-organic framework materials," The Journal of Chemical Physics 123, 014701 (2005), pp. 1-4.

Eun Young Lee, et al,, "Multifunctionality and crystal dynamics of a highly stable, porous metal-organic framework [$Zn_4O(NTB)_2$]" Journal of the American Chemical Society (2005) vol. 127, pp. 6374-6381.

Xiao-Jun Zhao et al., "A three-dimensional zinc trimesate framework: [$(CH_3)_2NH_2$] [$Zn(C_9H_3O_6)$] • ($C_3H_7NO$)," Applied Organometallic Chemistry (2005), vol. 19, pp. 694-695.

D. Maspoch, et al., "EPR characterization of a nanoporous metal-organic framework exhibiting a bulk magnetic ordering," Journal of Physics and Chemistry of Solids, (2005), vol. 65, pp. 819-824.

Xin-Long Wang, et al., "An unprecedented eight-connected self-penetrating network based on pentanuclear zinc cluster building blocks," Chem. Communication, (2005), pp. 4789-4791.

Xiuli Bai Yangguang Li, et al., "A novel three-dimensional hybrid framework based on fishbone-like copper halide inorganic units," Inorganica Chimica Acta 358, (2005), pp. 2571-2574.

Jorge Gonzalez, et al., "Deuterium NMR studies of framework and guest mobility in the metal-organic framework compound MOF-5, $Zn_4O(O_2CC_6H_4CO_2)_3$," Microporous and Mesoporous Materials 84, (2005), pp. 97-104.

Ru-Qiang Zou, et al., "Rational assembly of a 3D metal-organic framework for gas adsorption with predesigned cubic building blocks and 1D open channels," Chem, Commun., (2005) pp. 3526-3528.

Yi-Hang Wen, et al., Hydrothermal syntheses, crystal structures and characterizations of three new copper coordination polymers, Inorganica Chimica Acta 358 (2005) pp. 3347-3354.

Sujit K. Ghosh, et al., "Infinite chains of quasi-planar hexameric water clusters stabilized in a metal-organic framework built from $Co^{II}$ and pyrazine-2,3,5,6-tetracarboxylic acid," Eur. Journal of Inorganic Chemistry (2005), pp. 4880-4885.

Miguel Fuentes-Cabrera, et al., "Electronic structure and properties of isorcticular metal-organic frameworks: the case of $M$-IRMOF1 ($M$=Zn, Cd, Be, Mg, and Ca)," The Journal of Chemical Physics vol. 123, (2005), 124713, pp. 1-5.

Jianghua He, et al., "Synthesis, structure, and luminescent property of a heterometallic metal-organic framework constructed from rod-shaped secondary building blocks," Inorganic Chemistry, (2005) vol. 44, pp. 9279-9282.

Andrew R. Millward, et al., "Metal-organic frameworks with exceptionally high capacity for storage of carbon dioxide at room temperature," Journal of the American Chemical Society (2005), vol. 127, pp. 17998-17999.

Banglin Chen, et al., "Transformation of a metal-organic framework from the NbO to PtS net," Inorganic Chemistry, (2005), vol. 44, pp. 181-183.

Zhenqiang Wang, et al., "Ternary nets formed by self-assembly of triangles, squares, and tetrahedra," Angew. Chem. Int. Ed., (2005), vol. 44, pp. 2877-2880.

T, Yildirim, et al., "Direct observation of hydrogen adsorption sites and nanocage formation in metal-organic frameworks," Physical Review Letters, Nov. 18, 2005, vol. 95, 215504 pp. 1-4.

Danil N. Dybtsev, et al, "A Homochiral Metal-Organic Material with Permanent Porosity, Enantioselective Sorption Properties, and Catalytic Activity," Agnew. Chem. Int. Ed., 2006, 45, pp. 916-920.

Flachsbart, et al., "Design and fabrication of a multilayered polymer microfluidic chip with nanofluidic interconnects via adhesive contact printing," Lab-On-A-Chip, 6, 667-674, 2006.

Timothy M. Long, et al., "Water-Vapor Plasma-Based Surface Activation for Trichlorosilane Modification of PMMA," Langmuir vol. 22, No. 9, 2006, pp. 4104-4109.

Eliphas Wagner Simoes, et al., "Study of preconcentration of non-polar compounds in microchannels with constrictions," Sensors and Actuators B 115, 2006, pp. 232-239.

Ru-Qiang Zou, et al., "Strong fluorescent emission of a new fourfold-interpenetrated diamondoid metal-organic framework of zinc(II) urocanate with one-dimensional open channels," Microporous and Mesoporous Materials 91, 2006, 233-237.

Tong Ye, et al., "Ferroeletric Metal-or anic framework with a high dielectric constant," JACS, 2006, 128, pp. 6554-6555.

Banglin Chen, et al., "A microporous metal-organic framework for gas-chromatographic separation of alkanes," Angew. Chem. Int. Ed. 2006, 45, 1390-1393.

Pascal D. C. Dietzel, et al., "Hydrogen adsorption in a nickel based coordination polymer with open metal sites in the cylindrical cavities of the desolvated framework," Chemical Communication, 2006, pp. 959-961.

Lei Wang, et al., "Highly stable chiral cadmium 1,2,4-benzenetricarboxylate: Synthesis, structure, and NLO and fluorescence properties," Inorganic Chemistry, vol. 45, No. 6, 2006, pp. 2474-2478.

Feng Zheng, et al., "Single-Walled Carbon Nanotube Paper as a Sorbent for Organic Vapor Preconcentration," Analytical Chemistry, 2006, vol. 78, No. 7, pp. 2442-2446.

Rasmus Damgaard Poulsen, et al., "Solvothermal synthesis, multi-temperature crystal structures and physical properties of isostructural coordination polymers, $2C_4H_{12}N^+$-$[M_3(C_8H_4O_4)_4]^{2-}$$3C_5H_{11}NO$ $M$ = Co, Zn," Acta Crystallography (2006) B62, pp. 245-254.

Piotr Krawiec, et al., "Improved hydrogen storage in the metal-organic framework $Cu_3(BTC)_2$," Advanced Engineering Materials (2006) 8 No. 4, pp. 293-296.

Cameron J. Kepert, "Advanced functional properties in nanoporous coordination framework materials," Chemical Communication, (2006) pp. 695-700.

Long Pan, et al., "Separation of hydrocarbons with a microporous metal-organic framework," Angew. Chem. Int. Ed. (2006) vol. 45, pp. 616-619.

Shuangquan Zang, et al., "Interweaving of triple-helical and extended metal-o-metal single-helical chains with the same helix axis in a 3D metal-organic framework," Inorganic Chemist (2006), vol. 45, No. 10, pp. 3855-3857.

U. Mueller, et al., "Metal-organic framework—prospective industrial applications," Journal of Materials Chemistry, (2006) vol. 16, pp. 626-636.

Frank Stallmach, et al., "NMR studies on the diffusion of hydrocarbons on the metal-organic framework material MOF-5," Angew. Chem. Int. Ed. (2006), vol. 45, pp. 2123-2126.

Gyungse Park, et al., "Solvothermal synthesis, crystal structure, and magnetic properties of $[Co_3(SDA)_3(DMF)_2]$; 2-D layered metal-organic framework derived from 4,4' stilbenedicarboxylic acid ($H_2SDA$)," Bull. Korean Chem. Soc. (2006)., vol. 27, No. 3 .443-446.

Enrica Biemmi, et al,, "Synthesis and characterization of a new metal organic framework structure with a 2D porous system: $(H_2Net_2)$ $[Zn_3(BDC_4)]$ 3DEF," Solid State Sciences 8, (2006), pp. 363-370.

Suzy Surble, et al., "An EXAFS study of the formation of a nanoporous metal-organic framework: evidence for the retention of secondary building units during synthesis," Chem Commun., (2006) pp. 1518-1520.

Cheng-Zhi Xie, et al., "A novel 3D $Cu^1$metal-organic framework with middle-size channels despite the sixfold $ThSi_2$ interpenetrating topological structure," Eur. Journal of Inorganic Chemistry (2006) pp. 1337-1340.

Subhadip Neogi, et al., "Metal-organic frameworks of lanthanide (III) ions with a pod and bearing terminal carboxylates: Identification of water clusters of different nuclearity," Polyhedron 25 (2006) pp. 1491-1497.

C. Prestipino, et al. "Local structure of framework Cu(II) in HKUST-1 metallorganic framework: spectroscopic characterization upon activation and interaction with adsorbates," Chemical Materials, (2006), vol. 118, pp. 1337-1346.

Andrea C. Sudik, et al., "A metal-organic framework with a hierarchical system of pores and tetrahedral building blocks," Angew. Chem. Int. Ed., (2006), vol. 45, pp. 2528-2533.

Antek G. Wong-Foy, et al., "Exceptional $H_2$ saturation uptake in microporous metal-organic frameworks," Journal of the American Chemical Society (2006), vol. 128, pp. 3494-3495.

Jianghua He, et al., "Three metal-organic frameworks prepared from mixed solvents of DMF and HAc," Microporous and Mesoporous Materials, (2006), vol. 90, pp. 145-152.

Byunghoon Bae, et al., "A Touch-Mode Capacitance Microvalve Equipped with High Speed and Pressure Microsecond Switching Performance," MEMS 2006, Istanbul, Turkey, Jan. 22-26, 2006, pp. 766-769.

Patrick R. Lewis, et al., "Recent Advancements in the Gas-Phase MicroChemLab," IEEE Sensors Journal, vol. 6, No. 3, Jun. 2006, pp. 784-795.

Shaurya Prakash, et al., "Electroosmotic Flow in 'Click' Surface Modified Microfluidic Channels," Proceedings of ASME ICNMM2006, $4^{th}$ International Conference on Nanochannels, Microchannels and Minichannels, Jun. 19-21, 2006, Limerick, Ireland, Paper No. ICNMM2006-96153.

J. Yeom, et al., "Design and Characterization of Micropost-Filled Reactor for the Minimal Pressure Drop and Maximal-Surface-Area-to-Volume Ratio," Proceedings of IMECE 2006, 2006 ASME International Mechanical Engineering Congress and Exposition, Nov. 5-10, 2006, Chicago, Illinois, USA, IMECE2006-15836.

Zhuojia Lin, et al., "Microwave-Assisted Synthesis of Anionic Metal-Organic Frameworks Under Ionothermal Conditions," The Royal Society of Chemistry 2006, Chem. Commun., 2006, pp. 2021-2023.

N. Rajic, et al., "An Evidence for a Chain to Network Transformation During the Microwave Hydrothermal Crystallization of an Open-Framework Zinc Terephthalate," J. Porous Mater. 2006, vol. 13: pp. 153-156.

Ioana Voiculescu, et al., "Micropreconcentrator for Enhanced Trace Detection of Explosives and Chemical Agents," IEEE Sensors Journal, vol. 6, No. 5, Oct. 2006, pp. 1094-1104.

Bae, B. et al., A touch-mode capacitance microvalve equipped with high speed and pressure microsecond switching performance, MEMS 766-769 (2006).

Bochobza-Degani, O. et al., On the effect of residual charges on the pull-in parameters of electrostatic actuators, Sensors and Actuators A 97-98:563-568 (2002).

Bosch, D. et al., A silicon microvalve with combined electromagnetic/electrostatic actuation, Sensors and Actuators 37-38:684-692 (1993).

Castañer, L. M. et al., Pull-in time-energy product of electrostatic actuators: comparison of experiments with simulation, Sensors and Actuators, 83:263-269 (2000).

Legtenberg, R. et al., Electrostatic Curved Electrode Actuators, Journal of Microelectromechanical Systems 6(3):257-265 (1997).

Messner, S. et al., 3-way silicon microvalve for pneumatic applications with electrostatus actuation principle, Microfluid Nanofluid 89-96 (2006).

Messner, S. et al., Electrostatic driven 3-way silicon microvalve for pneumatic applications, IEEE 88-91 (2003).

Oberhammer, J. et al., Design and fabrication aspects of an S-shaped film actuator based DC to RF MEMS switch, Journal of Microelectromechanical Systems 13(3):421-428 (2004).

Ohnstein, T. et al., Micromachined silicone microvalve, Proc. IEEE Micro Electro Mechanical Systems, An Investigation of Micro Structures, Sensors, Actuators, Machines and Robots, Napa Valley, CA 95-98 (1990).

Philpott, M. L. et al., Switchable electrostatic micro-valves with high hold-off pressure, Technical Digest of the 2000 Solid-State Sensor and Actuator Workshop, 226-229, (2000).

Sato, K. et al., An electrostatically actuated gas valve with an S-shaped film element, J. Micromech. Microeng. 4:205-209 (1994).

Schaible, J. et al., Electrostatic microvalves in silicon with 2-way-function for industrial applications, The $11^{th}$ International Conference on Solid-State Sensors and Actuators, Munich, Germany 928-931 (2001).

Shikida, M. et al., Characteristics of an electrostatically-driven gas valve under high-pressure conditions, Center for Materials Processing Technology 235-240 (1994).

Shikida, M. et al., Electrostatically driven gas valve with high conductance, Journal of Microelectromechanical Systems, 3(2):76-80 (1994).

Shikida, M. et al., Fabrication of an S-shaped microactuator, Journal of Microelectromechanical Systems, 6(1):18-24 (1997).

Shikida, M. et al., Micromachined S-shaped actuator, Sixth International Symposium on Micro Machine and Human Science 167-172 (1995).

Shikida, M. et al., Response time measurement of electrostatic S-shaped film actuator related to environmental gas pressure conditions, IEEE 210-215 (1996).

Vandelli, N. et al., Development of a MEMS microvalve array for fluid flow control, Journal of Microelectromechanical Systems 7(4):395-403 (1998).

Yang, X. et al., An electrostatic, on/off microvalve designed for gas fuel delivery for the MIT microengine, Journal of Microelectromechanical Systems, 13(4):660-668 (2004).

Huff et al., A pressure-balanced electrostatically-actuated microvalve, Technical Digest, 1990 Solid-State Sensor and Actuator Workshop, pp. 123-127 (1990).

* cited by examiner

Panel A

Panel B

Panel C

Panel D

Panel A

Panel B

Panel A

Panel B

Panel C

Panel D

Panel A

Panel B

Panel A                    Panel B

Panel A   Panel B

COLUMN DESIGN FOR MICRO GAS CHROMATOGRAPH

CROSS-REFERENCES TO RELATED APPLICATIONS

This application claims priority to and benefit under 35 U.S.C. §119(e) to U.S. Provisional Application Ser. Nos. 61/021,588 and 61/021,620, both filed Jan. 16, 2008, the disclosures of which are herein incorporated by reference in their entirety.

STATEMENT AS TO RIGHTS TO INVENTIONS MADE UNDER FEDERALLY SPONSORED RESEARCH OR DEVELOPMENT

This invention was made, at least in part, with U.S. government support under the Defense Advanced Research Projects Agency (DARPA) under U.S. Air Force Grant F A8650-04-1-7121. The Government has certain rights in this invention.

BACKGROUND OF THE INVENTION

1. Field of the Invention

The invention relates generally to novel micro-column designs for micro-gas chromatography ($\mu$GC) micro-columns, such as serpentine micro-columns, which give relatively lower height equivalent to theoretical plate (HETP) values. Turns are a major dispersion source for serpentine configuration and sinusoidal compensation structures following the turns may result in the lowest dispersion.

2. Related Art

A gas chromatograph (GC) is a chemical analysis instrument used for separating chemicals in a complex sample and is generally composed of three basic parts, an injector, a column, and a detector. Different chemical constituents of a sample pass in a gas stream through the column at different rates depending on their various chemical and physical properties and their interaction with a specific column filling, called the stationary phase. As the chemicals exit the end of the column, they are detected and identified electronically. Conventional GC columns are generally small open tubes with internal diameters in the range of about 270 microns to about 530 microns and lengths bout in the range of about 10 meters to 30 meters. The inside walls of these columns are coated with a thin even layer of organic polymer, the stationary phase, to a thickness of less than about one micron.

Conventional GCs are very bulky and are not small enough to be carried by individuals. Therefore, many efforts are being made to develop a GC that is highly miniaturized and portable, a so-called microfabricated GC ($\mu$GC). Micro-columns are the heart of the GC technique and several studies have considered microelectromechanical systems (MEMS) columns for $\mu$GC's. Previous work on $\mu$GC, however, has concentrated on columns that are arranged with a spiral geometry as shown in FIG. 1, Panel A. Research done by applicants indicates that the spiral channel configuration may not be well suited for microanalytical system, as discussed below.

Therefore, a need remains for a microfabricated GC column that minimizes band broadening, enables long column lengths with low pressure drop, enables uniform stationary phase coatings, and provides a column configuration that can be easily integrated with other microfabricated components to provide a compact and fast microanalytical system.

SUMMARY OF THE INVENTION

The invention provides improved column channel structures and methods for producing channel structures suitable for use in $\mu$GC. In particular, the columns may be constructed using a particular channel structure, such as a serpentine channel structure, having various bend geometries for $\mu$GC separation, resulting in good $\mu$GC resolution.

According to one aspect of the invention, a microfabricated gas chromatography (GC) column for separation of analytes in a gas mixture may include a substrate having a top surface and a bottom surface, a plurality of adjacent channels in the substrate top surface, each channel having a generally serpentine configuration and including a plurality of bends where the spacing between adjacent channels is less than about 4 times a diameter of the column. In particular, one of the channels diameter of a channel is in a range of about 20 microns to about 1000 microns.

The substrate may be composed of metals, polymers, glasses, ceramics including silicon, glass, polyimide, silicon carbide, PDMS, nickel tantalium, titanium, and copper, for example.

The bend may have a configuration such as a circular bend, a circular bend with a sine wave compensation, a conically converging turn, and a concentrically converging turn. Specifically, the corner of the bend in the channel may be rounded.

The channels may be coated with stationary phase compound having a thickness. The wall of the channel may be smoothened to at least one tenth of the stationary phase thickness. Specifically, the phase thickness may be about 100 nm and the wall of the channel may be smoothened to about 10 nm. Moreover, the radius of a corner of the channel may be rounded off to be at least 10 times larger than a thickness of a stationary phase coating the channels.

The substrate may include top and bottom wafers, each having a top and bottom surface therein. The plurality of adjacent channels may be disposed in the top and the bottom wafer such that when the wafers are adjacent to each other, said channels from the top wafer are aligned with channels from the bottom wafer to define the column. Moreover, the plurality of bends may be rounded.

According to another aspect of the invention, a process for fabricating a micro-fabricated gas chromatography column for separation of analytes in a gas mixture may include providing a substrate, etching a channel in the substrate to generate a plurality of channels having a serpentine configuration and having a plurality of bends, smoothening a plurality of walls of the channels, and rounding off a plurality of corners of the plurality of channels. Additionally, the process may further include coating the microfabricated gas chromatography column with a stationary phase compound. The substrate may be composed of a material such as metals, polymers, glasses, ceramics including silicon, glass, polyimide, silicon carbide, PDMS, nickel tantalium, titanium, and copper.

The channels in the generating step may be created by a process such as deep reactive ion-etching (DRIE), laser milling, wet etching, photolithography, molding hot pressing and photoforming. The smoothening may be performed by a process such as electrochemical etching and buffered oxide etching (BOE), for example. The rounding step may be performed by a process such as oxidation and wet chemical etching, electrochemical etching and wet etching, molding, coating with a polymer or glass, and anisotropic etching.

Additional features, advantages, and embodiments of the invention may be set forth or apparent from consideration of the following detailed description, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced.

DETAILED DESCRIPTION OF THE INVENTION

Figure 1:
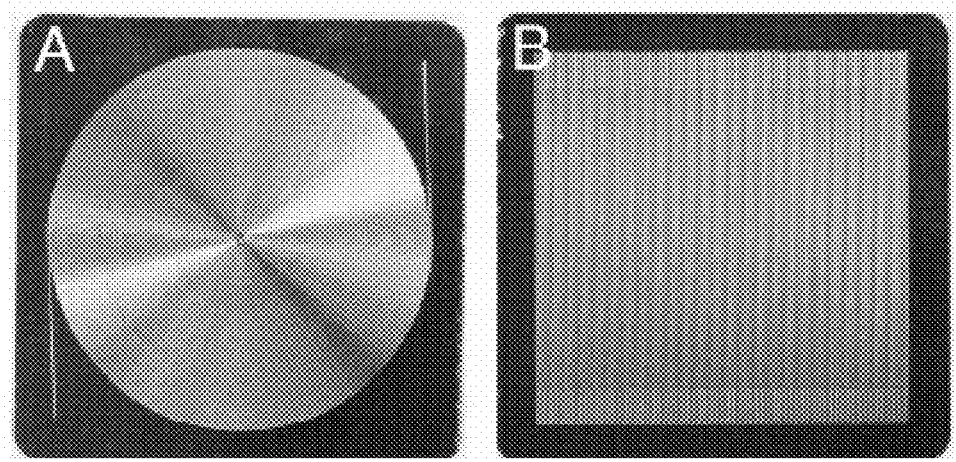
FIG. 1 is a photograph of two column configurations. Panel A is a photograph of a spiral micro-column. Panel B is a photograph of a serpentine micro-column constructed according to principles of the invention.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is noted that as used herein and in the appended claims, the singular forms "a," "an," and "the" include the plural reference unless the context clearly dictates otherwise. Thus, for example, a reference to "a bend" is a reference to one or more bends and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Accordingly, provided immediately below is a "Definition" section, where certain terms related to the invention are defined specifically for clarity, but all of the definitions are consistent with how a skilled artisan would understand these terms. Particular methods, devices, and materials are described, although any methods and materials similar or equivalent to those described herein can be used in the practice or testing of the invention. All references referred to herein are incorporated by reference herein in their entirety.

DEFINITIONS

BOE is Buffered Oxide Etch
DRIE is Deep Reactive Ion Etching
GC is Gas Chromatograph
HETP is Height of a Theoretical Plate Values
MEMS is MicroElectroMechanical Systems
μGC is Microfabricated Gas Chromatograph
OD is Optical Density
RIE is Reactive Ion Etching
TZ is Trennzahl Number (also known as separation number)
N is the number of theoretical plates The term "Dean Number," as used herein, generally refers to a function of gas flow rate, the gas pressure, and the gas velocity. The Dean number may be calculated for hydrogen at about 1 atmosphere of pressure at rate of about 50 cm/second. The Dean number is typically denoted by the symbol D, and is defined as $D=(\rho U a/\mu)(a/R)^{1/2}$ where $\rho$ is the density of the fluid, $\mu$ is the dynamic viscosity, U is the axial velocity scale, a is a typical lengthscale associated with the channel cross-section (eg radius in the case of a circular pipe or hydraulic radius for a channel with a rectangular cross section), R is the radius of curvature of the path of the channel. The Dean number is therefore the product of a Reynolds number (based on axial flow U through a pipe of radius a) and the square root of the length scale ratio a/R.

The term "spiral" as used herein, generally refers to a column consisting of a series of channels, where the channels wind around a fixed point such that the distance from the fixed point is increasing or decreasing.

The term "serpentine," as used herein, generally refers to a column consisting of parallel channels with similar lengths connected by curved sections at the end of each channel.

Figure 2:
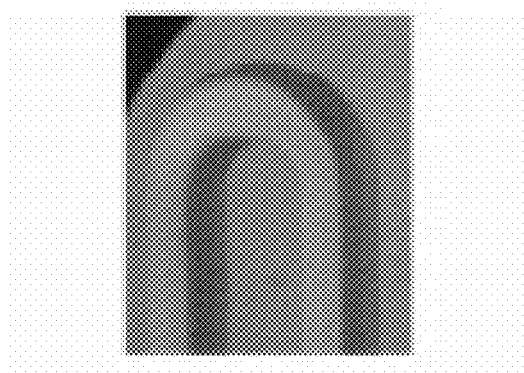
FIG. 2 are photographs showing bend geometries that may be used for constructing the analytical micro-columns of the invention. Panel A is a photograph showing circular bends. Panel B is a photograph showing sine wave bends. Panel C is a photograph showing conically converging bends. Panel D is a photograph showing concentrically converging bends.
Figure 2:
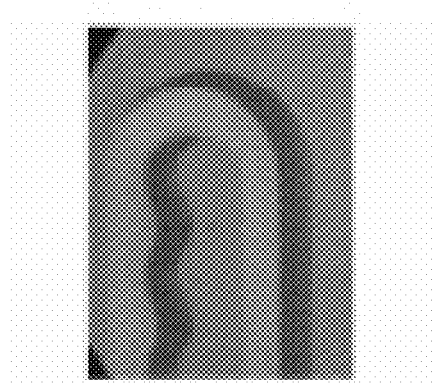
Figure 2:
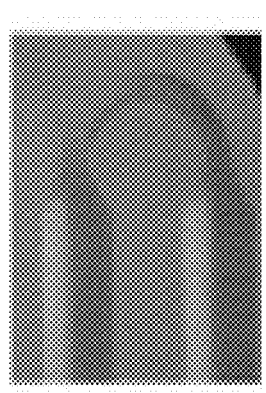
Figure 2:
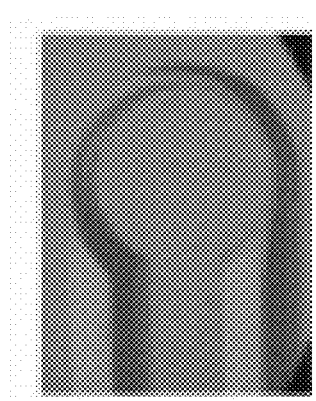

The invention relates generally to micro-columns and methods for producing micro-columns for use in μGCs. In particular, the analytical micro-columns may be constructed using particularly advantageous channel structures, such as a serpentine channel structure, having various bend geometries for enhancing μGC separation. The geometric bends may include circular bends (FIG. 2, Panel A), sine wave bends (FIG. 2, Panel B), conically converging bends (FIG. 2, Panel C), and concentrically converging bends (FIG. 2, Panel D), for example. Additionally, the micro-column fabrication process may create sharp bends in the channel structure, which may negatively effect the resolution of the GC. Therefore, if desired, the radius of the bend may be reduced by rounding off the bottom of the bend in the channel structure.

In some specific embodiments, the micro-column geometry may be a serpentine channel structure. The serpentine channel structure is advantageous because it results in higher separation performance in isothermal or temperature programmed modes. In particular, the serpentine channel structure shows lower band broadening for retained solutes in isothermal modes of operation compared to circular or square spiral configurations. The advantage of using serpentine micro-column configurations in temperature programmed modes is clearly evident in the average velocity range of about 15 cm/s to about 40 cm/s, as discussed below. Also, faster elution of retained species is obtained with the serpentine micro-column configurations indicating that thinner stationary phase coatings are obtained on serpentine designs as compared to spiral designs when the coating parameters are kept constant, also discussed below.

Figure 3:
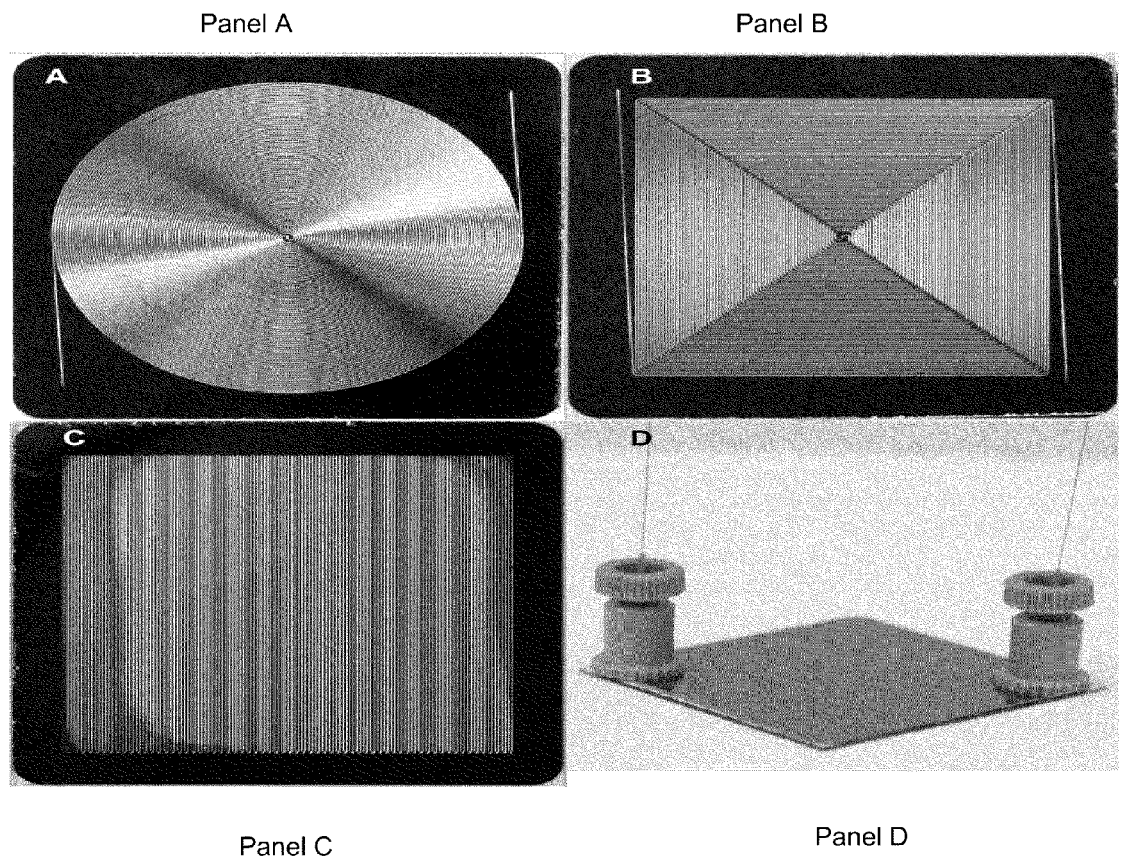
FIG. 3 shows photographs of three different silicon-Pyrex® micro-column configurations that were fabricated according to principles of the invention. Panel A shows a circular spiral configuration, Panel B shows a square spiral configuration, and Panel C shows a serpentine configuration. Each micro-column is 3 m long, 100 µm wide and 100 µm deep in cross-section. The resultant chip size was 3.4 cm×3.4 cm. Panel D shows the packaged micro-column with epoxied Nanoports® connecting the Restek (#560292) deactivated guard capillaries (I.D. 100 µm, O.D. 200 µm) to the micro-column.
Figure 4:
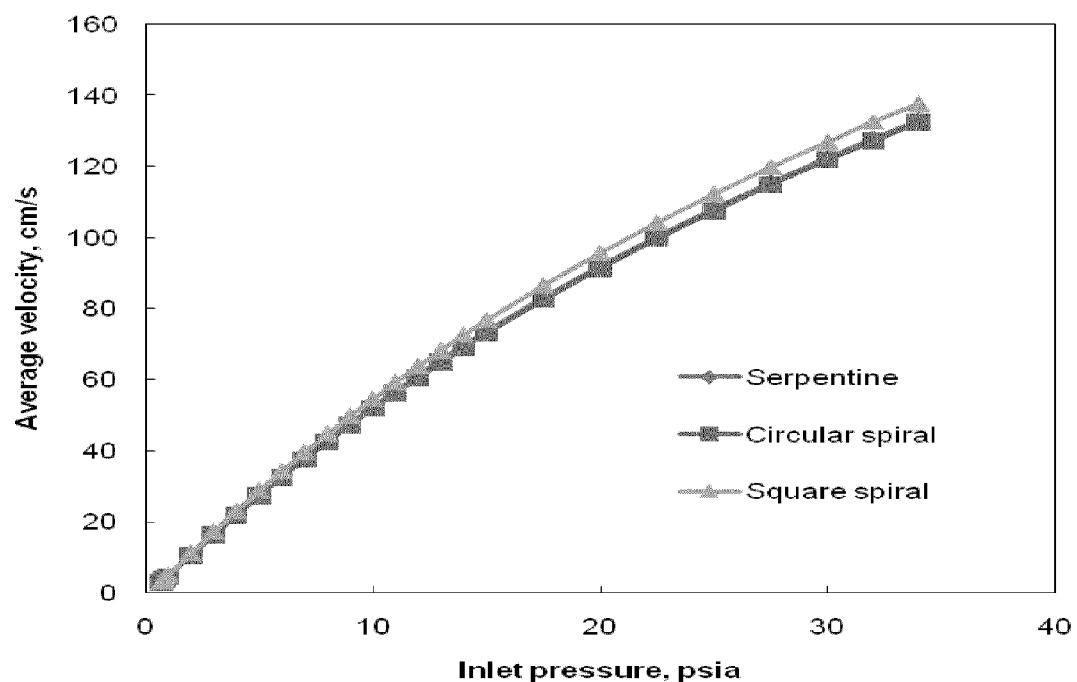
FIG. 4 is a graph showing the average gas carrier velocity versus inlet pressure for the three different uncoated micro-column configurations, serpentine, circular spiral, and square spiral shown in FIG. 3. The average carrier gas velocity was calculated using the methane retention time. The data points represent the average reading from two chips of each configuration. The error bars in the plots represent the deviation in the gas velocity obtained within the set of chips tested, which was typically less than 1% and is hard to visualize on the plot.

FIG. 3, Panels A-C, shows photographs of three different silicon-Pyrex® micro-column configurations that were fabricated according to principles of the invention: circular spiral (FIG. 3, Panel A), square spiral (FIG. 3, Panel B) and serpentine (FIG. 3, Panel C). Each micro-column in FIG. 3 was 3 m in length, 100 μm wide, and 100 μm deep in cross-section. The resultant chip size was 3.4 cm×3.4 cm. These three different micro-column configurations were tested for their average carrier gas velocity using methane injections, using the methods described in Specific Example 5. FIG. 4 shows the average carrier gas velocity in the different uncoated micro-column configurations at different column inlet pressures. As shown in FIG. 4, the difference between average gas velocity on serpentine and circular spiral micro-columns was found to be less than about 1.5% in the range of inlet pressure tested. The square spiral gave slightly higher average velocity (about 6%) than the other two configurations.

Figure 5:
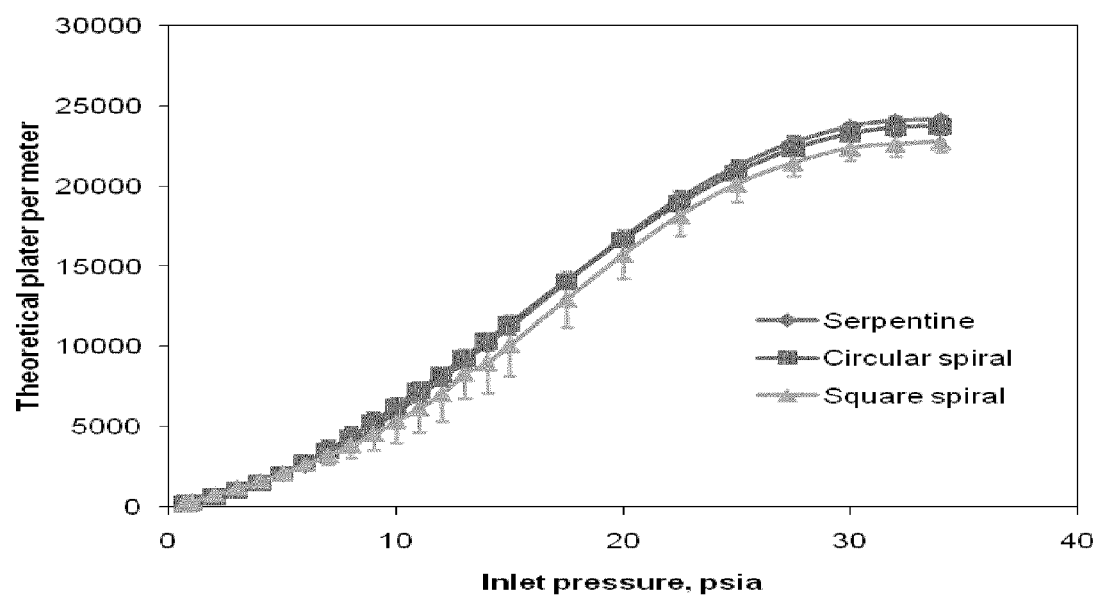
FIG. 5 is a graph showing the number of theoretical plates generated for unretained peak (methane) elution versus inlet pressure for the different uncoated micro-column configurations (serpentine, square spiral, and circular spiral) shown in FIG. 3. Hydrogen was used as the carrier gas. The error bars indicated the deviation in results from the set of chips of each micro-column configuration. N was used to measure the difference in band broadening induced by the micro-column-GC setup. The points in the plot represent the average N value and the error bars express the difference in the values recorded from chips with same configuration. The deviation in N values for serpentine and circular spiral micro-columns was found to be small (0.3-12%). Comparatively the deviations in N values for the square spiral micro-columns were found to be higher (0.5-38%). The deviations for square spiral micro-column data were higher in the 10 to 25 psi range.
Figure 6:
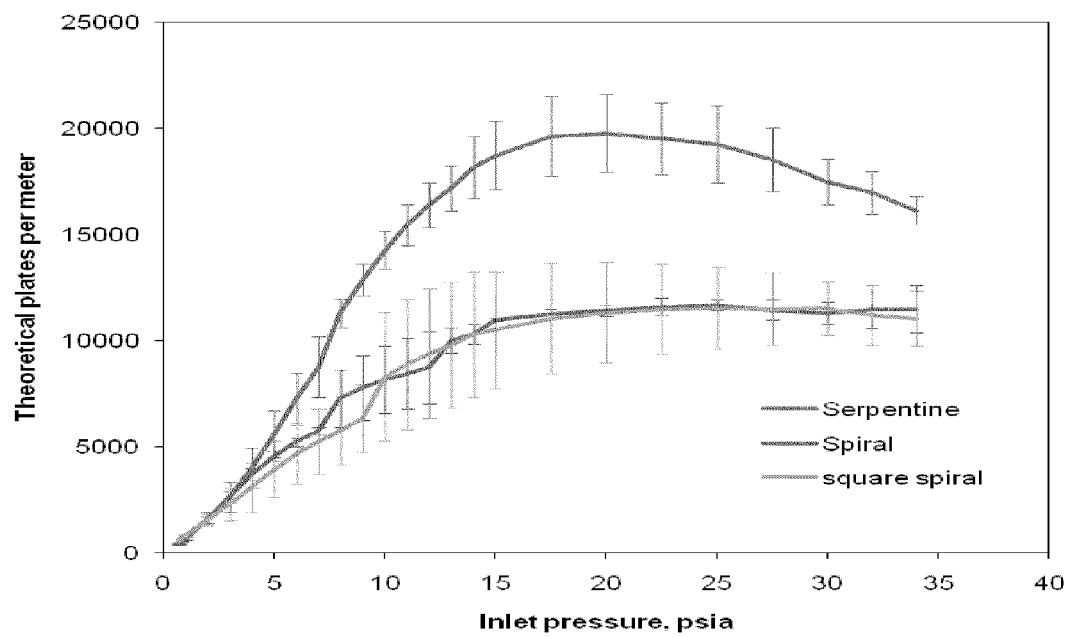
FIG. 6 is a plot showing the theoretical plate height for slightly retained solute (iso-octane at 40° C.) versus inlet pressure with different uncoated micro-column configurations shown in FIG. 3. Hydrogen was used as the carrier gas. 1 µl of headspace vapor was injected with a split of 500:1 (injector temperature 250° C.); the micro-column was held at 40° C. The points represent the average value of theoretical plates obtained from two different micro-column chips of each configuration (serpentine, square spiral, and circular spiral). The error bars indicate the deviation in results within each configuration. The deviations in results were highest for the square spiral micro-columns and lowest for the circular spiral micro-columns. The deviations in plate number per meter within each configuration were as high as nearly 1800, 1700, and 3000 plates for serpentine, circular spiral and square spiral designs respectively.

In order to study the efficacy of separation in each of the micro-column configurations shown in FIG. 3, the number of theoretical plates was determined for each of the different micro-column configurations. As appreciated by those of skill in the art, a micro-column having more theoretical plates, increases the efficacy of the separation process. Accordingly, the number of theoretical plates (N) per meter were generated for a methane and isooctane pulse for each of the three different micro-column configurations shown in FIG. 3. FIGS. 5 and 6 show the number of theoretical plates (N) generated per meter for a methane and isooctane pulse respectively, on the three different micro-column configurations as a function of inlet pressure. The points on the plot represent the average N value and the error bars express the difference in values recorded from silicon ships with the same configuration. FIG. 5 shows that the serpentine and circular spiral micro-columns gave closely comparable number of theoretical plates with methane tracer tests over the tested inlet pressure range of about 0.7 to about 34 psi; however, square spiral micro-columns gave a slightly lower number of theoretical plates. To compare, at about 15 psi inlet pressure the number of theoretical plates per meter for serpentine and circular spiral micro-columns were about 11200 and about 11400, respectively, while square spiral micro-columns resulted in about 10100 plates per meter. In all three of the micro-column configuration studied, the theoretical plate numbers increased with the inlet pressure and then plateaued after about 30 psi.

As shown in FIG. 6, the serpentine micro-column gave higher number of theoretical plates compared to the spiral designs when isooctane was used as a tracer. In the latter case, circular spiral and square spiral micro-columns gave closely comparable values for the average number of theoretical plates. To compare, at about 15 psi inlet pressure, the serpentine micro-columns resulted in about 18700 plates per meter while circular spiral and square spiral micro-columns resulted in about 11000 and 10500 plates per meter, respectively. In the case of the two spiral configurations tested, the theoretical plate numbers increased and plateaued after about 15 psi inlet pressure, whereas for the serpentine configurations, the theoretical plate numbers increased with the inlet pressure and gradually started decreasing about 20 psi onwards.

Figure 7:
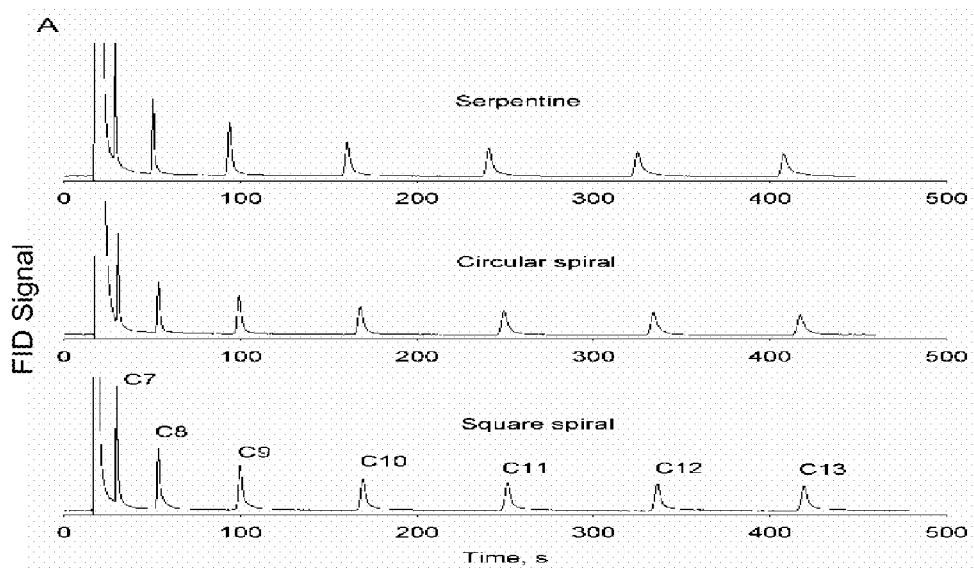
FIG. 7 shows two sets of three chromatograms of a n-$C_5$ to n-$C_{13}$ mixture on 3-m-long micro-columns of serpentine, circular spiral, and square spiral configurations shown in FIG. 3. 1 µL of the liquid mix was injected with a split of 500:1 (injector temperature 250° C.). The data shown corresponds to experiments using an average carrier gas velocity of 26 cm/s, shown in Panel A and 40 cm/s shown in Panel B. A temperature ramp rate of 10° C./min was used with the starting and final temperature of 30° C. and 140° C., respectively.
Figure 7:
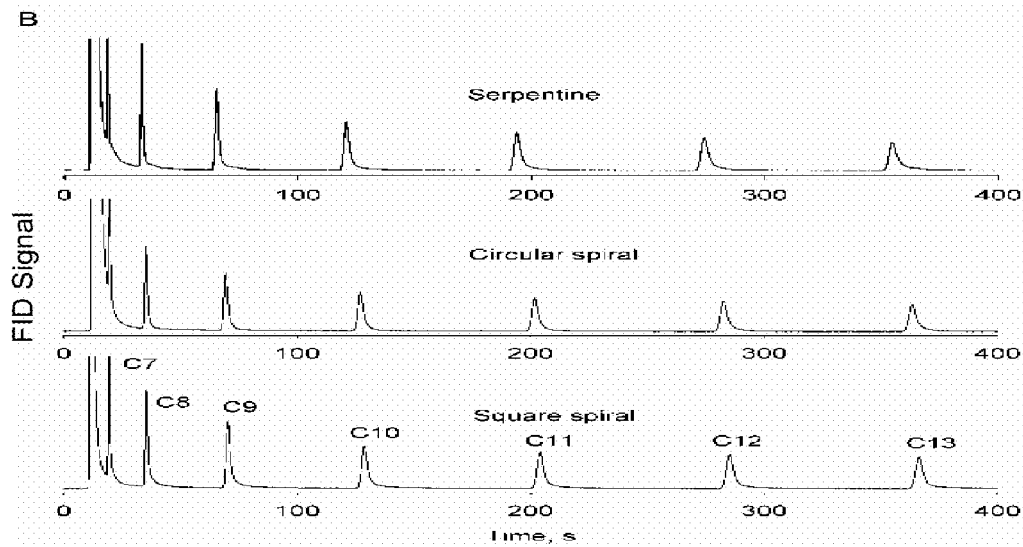

The effect of carrier gas inlet pressure and temperature ramp rate on temperature-programmed separation on coated micro-columns having the configurations shown in FIG. 3 was studied. The surface of the three micro-column configurations of the invention were coated with 5% phenyl polydimethylsiloxane stationary phase (OV-5 vi, Ohio valley specialty chemicals). FIG. 7 shows temperature-programmed separation chromatograms of n-$C_7$ to n-$C_{13}$ mixture on the coated micro-columns of the different configurations of the invention at two different carrier gas velocities, about 26 cm/s shown in FIG. 7, Panel A and about 40 cm/s shown in FIG. 7, Panel B. As shown in FIG. 7, peak shapes were good on all the three micro-columns of the invention with minimal signs of tailing and no artifacts. The n-alkane peaks were seen to elute faster on the serpentine micro-column compared to the spiral configurations. Among the spiral configurations (i.e., circular spiral and square spiral), the circular spiral configuration resulted in faster eluting peaks compared to square spiral; however, the difference was less when compared to serpentines and spirals. To compare, at carrier gas velocity of about 26 cm/s (FIG. 7, Panel A) the $C_{11}$ peak elutes at 240.6 s on the serpentine micro-column compared to 249.3 s and 251.04 s on the circular and square spiral micro-columns, respectively. A similar trend was also observed at carrier gas velocity of about 40 cm/s (FIG. 7, Panel B); the $C_{11}$ peak elutes at 193.74 s, 201.78 s, and 204.3 s on the serpentine, circular spiral, and square spiral configurations, respectively.

Figure 8:
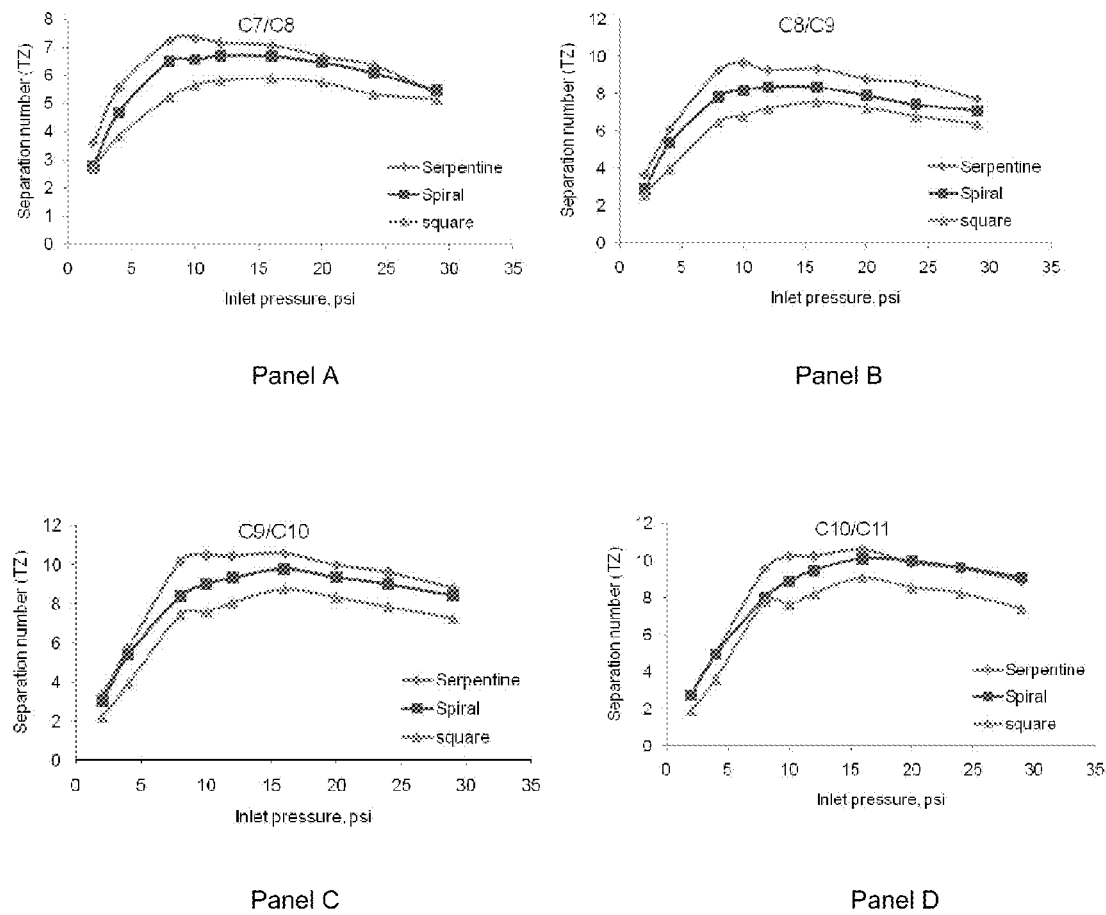
FIG. 8 shows four plots of the separation number (TZ) versus inlet pressure for four different alkane pairs on the three micro-column configurations shown in FIG. 3. The starting and final temperatures were 30° C. and 140° C., respectively. A temperature ramp rate of 10° C./min was used. Panel A is a plot showing C7/C8 separation; Panel B is a plot showing C8/C9 separation; Panel C is a plot showing C9/C10; and Panel D is a plot showing C10/C11 separation.

Moreover, a more detailed analysis was carried out on the different micro-column configurations of the invention by calculating the separation numbers (TZ) for the consecutive peak pairs at different inlet pressure conditions for each of the configurations. As discussed below, the serpentine micro-columns resulted in higher separation numbers than either of the circular spiral or square spiral micro-column configurations. FIG. 8 shows the plot of TZ as a function of carrier gas inlet pressure for the $C_7/C_8$ (Panel A), $C_8/C_9$ (Panel B), $C_9/C_{10}$ (Panel C), and $C_{10}/C_{11}$ (Panel D) alkane pair elution on the different micro-column configurations. The separation numbers in all cases followed a similar trend. For example, TZ values were found to increase rapidly with the inlet pressure until maxima was reached and decreased slowly. Table 1, below, lists the maximum TZ obtained and its corresponding inlet pressure on the tested micro-column configurations with the different alkane pairs. Table 1 shows the maximum separation number and in parentheses, the pressure at which the separation number was obtained.

TABLE 1

| | Alkane pair | | | |
|---|---|---|---|---|
| Configuration | C7/C8 | C8/C9 | C9/C10 | C10/C11 |
| Serpentine | 7.33 (10) | 9.65 (10) | 10.56 (16) | 10.56 (16) |
| Circular spiral | 6.7 (12) | 8.34 (12) | 9.8 (16) | 10.12 (16) |
| Square spiral | 5.9 (16) | 7.54 (16) | 8.74 (16) | 9.08 (16) |

As shown in FIG. 8, the serpentine micro-columns were found to achieve higher separation numbers compared to the spiral micro-columns, and the circular spiral micro-column resulted in higher separation numbers compared to the square spiral configuration. It was also noted that serpentine micro-column achieved its maximum separation numbers at lower inlet pressure of about 10 psi for the $C_7/C_8$ and $C_8/C_9$ alkane pairs compared to about 12 psi and about 16 psi for the circular and square spiral configurations, respectively. Serpentine micro-columns resulted in higher separations numbers than the circular-spiral micro-column in the inlet pressure range of 6-16 psi for four alkane pairs compared. To illustrate, at 10 psi the TZ values for the $C_9/C_{10}$ pair were found to be 10.47, 8.87 and, 7.58 on the serpentine, circular-spiral and square-spiral configurations, respectively.

Figure 9:
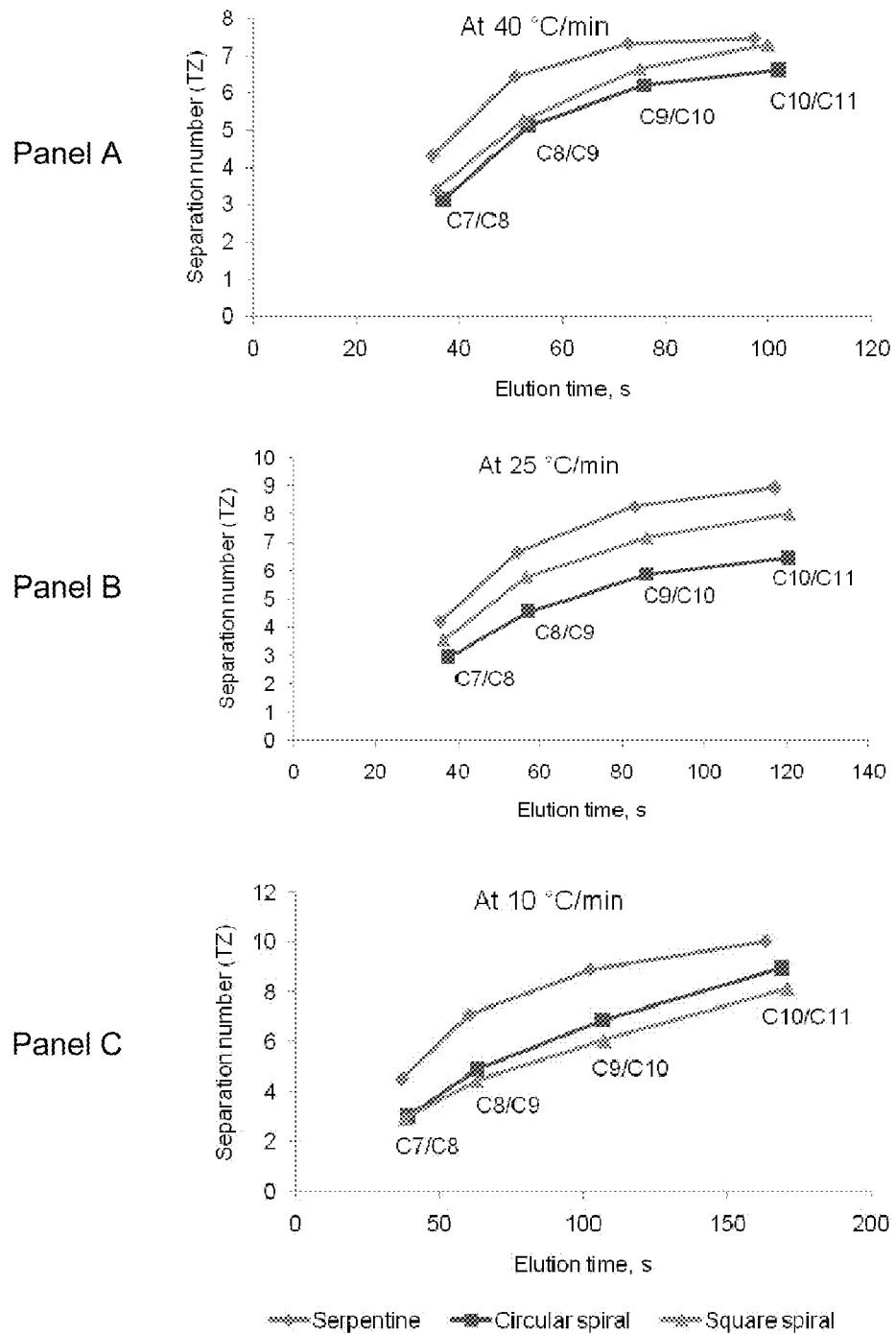
FIG. 9 shows three plots of separation numbers (TZ) for n-alkane pairs versus the retention times for the heavier alkane of the pair for the three different configurations (circular spiral, square spiral, and serpentine) shown in FIG. 3. Data was extracted from the temperature-programmed separation chromatograms of n-$C_5$ to n-$C_{12}$ mixture at three different ramp rates for the three micro-column configurations. The starting and final temperatures for the separation were 30° C. and 140° C., respectively. The numbers on the plots represent the temperature ramp rate used for the separation. The respective ramp rates are as follows: Panel A is 40° C./min, Panel B is 25° C./min, and Panel C is 10° C./min.

FIG. 9 shows plots of the separation numbers for the different alkane pairs (i.e., $C_7/C_8$, $C_8/C_9$, $C_9/C_{10}$, and $C_{10}/C_{11}$) separated on different micro-column configurations of the invention at three temperature ramp rates of 10° C./min, 20° C./min, and 40° C./min, Panels A, B, and C, respectively. The X-axis of the plot indicates the elution time for the heavier alkane of the pair. The TZ value for a particular alkane pair was found to decrease as the ramp rate increases for all configurations tested. As the alkane pair got heavier the TZ value increased for each configuration at all ramp rates. The peaks were found to elute faster on serpentine micro-columns with all temperature ramp rates and the difference was more apparent with the heavier alkanes. Serpentine micro-columns resulted in higher separation numbers compared to the spiral configurations with the three ramp rates tested. For example, the separation numbers at the temperature ramp rate of 25° C./min for the $C_9/C_{10}$ pair on the serpentine, circular-spiral and square-spiral configurations were calculated to be 8.27, 7.18, and 5.87, respectively. It was found that the circular spiral micro-columns gave higher separation numbers than square spiral micro-column at 25 and 40° C./min, while square spiral micro-columns resulted in higher separation numbers at 10° C./min. To exemplify, the separation numbers for C9/$C_{10}$ pair for the circular-spiral and square-spiral were calculated to be 6.87 and 6.06 at 10° C./min, 5.87 and 7.18 at 25° C./min, and 6.19 and 6.65 at 40° C./min.

A study was conducted to determine the resolution of peaks of a 33 component mix (components listed in Table 2, below) in the three micro-column configurations of the invention.

TABLE 2

| | | Resolution | | |
|---|---|---|---|---|
| No. | Compound | Serpentine | Circular spiral | Square spiral |
| 1 | Benzene | | | |
| 2 | Heptane | | | |
| 3 | 3-Pentanone | | | |
| 4 | Toluene | | | |
| 5 | Octane | | | |
| 6 | 2-Hexanone | | | |
| 7 | Chlorobenzene | | | |
| 8 | Ethylbenzene | | | |
| 9 | m-Xylene | | | |
| 10 | Styrene | | | |
| 11 | Nonane | 1.10 | 0.64 | 0.97 |
| 12 | 1,4-Dichlorobutane | 0.52 | 0.88 | 0.35 |
| 13 | α-Pinene | 1.65 | 1.08 | 1.48 |
| 14 | 1-Bromohexane | 0.43 | 0.56 | 0.31 |
| 15 | 3-Chlorotoluene | 1.37 | 1.54 | 1.17 |
| 16 | 1,3,5-Trimethylbenzene | 1.48 | 1.36 | 1.31 |
| 17 | 1,2,4-Trimethylbenzene | 2.06 | 1.85 | 1.81 |
| 18 | 1,3-Dichlorobenzene | 0.71 | NR | 0.67 |
| 19 | Decane | 0.56 | NR | 0.51 |
| 20 | Limonene | 1.85 | 1.30 | 1.61 |
| 21 | 1-Chlorooctane | 3.55 | 2.75 | 3.08 |
| 22 | Terpinolene | 2.20 | 1.47 | 1.88 |
| 23 | Undecane | 1.98 | 1.21 | 1.70 |
| 24 | 1,6-Dichlorohexane | 2.35 | 2.11 | 1.97 |
| 25 | 2-Ethoxyphenol | 2.02 | NR | NR |
| 26 | Naphthalene | 0.35 | NR | NR |
| 27 | 4-Decanone | | | |
| 28 | Dodecane | | | |
| 29 | 2-Decanone | | | |
| 30 | 6-Undecanone | | | |
| 31 | Tridecane | | | |
| 32 | Carvacrol | | | |

Figure 10:
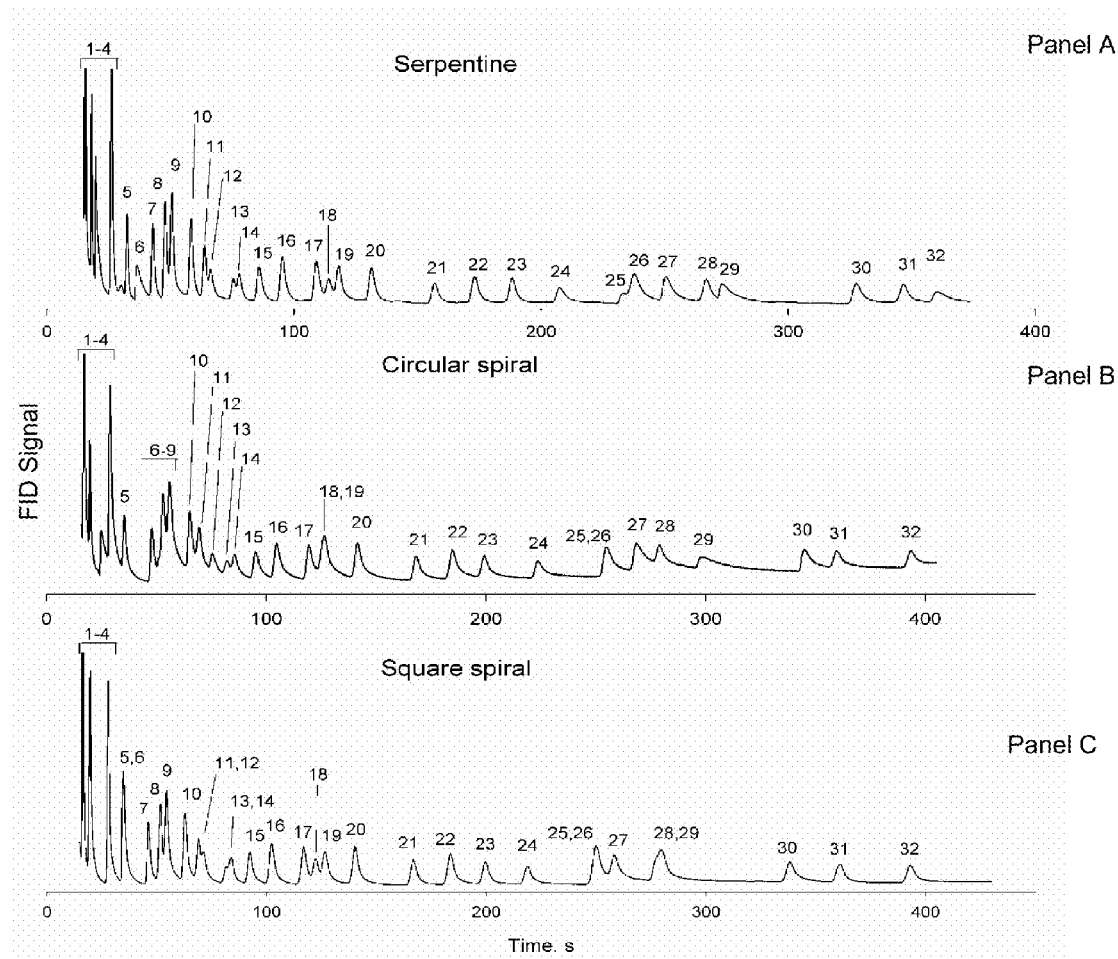
FIG. 10 shows three chromatograms showing temperature-programmed separation of the 33 component mix (described in Table 1) obtained on the three micro-column configurations shown in FIG. 3. 1 µL liquid mixture was injected with a split of 500:1 (injector temperature of 250° C.). The starting and final temperature of 30° C. and 140° C. was used. The temperature ramp rate was set to 10° C./min. Hydrogen was used as the carrier gas. The average carrier gas velocity was set to 40 cm/s. Panel A shows separation on a serpentine micro-column, Panel B shows separation on a circular spiral micro-column, and Panel C show separation on a square spiral micro-column.

FIG. 10 shows the temperature-programmed separation of the 33 component mix on the three micro-column configurations shown in FIG. 3. As shown in FIG. 10, the peaks eluted faster (last peak at 360.6 s) on the serpentine design compared to the spiral configurations (last peak at 393.6 s and 394.2 s for the circular and square spiral respectively) under the same operating conditions. Peaks 6 and 25 corresponding to 2-hexanone and 2-ethoxyphenol respectively showed a different elution sequence on the three micro-column configurations. The 2-hexanone peak (6) elutes at 36.6 s on the serpentine micro-column as a distinct peak between the octane (5) and chlorobenzene (7) peaks at 32.52 s and 42.96 s; while peak 6 co-elutes with peak 8 on the circular spiral micro-column and with peak 5 on the square spiral micro-column. The 2-ethoxyphenol peak (25) elutes at 3.89 s on the serpentine micro-column, just before the naphthalene peak (26); while peak 25 elutes irresolvably at the tailing end of the peak 26 on the circular spiral micro-column and co-elutes with peak 26 on the square spiral micro-column. Peak resolution analysis was performed on the peak 10 to 26 and reported in Table 2, below. The resolution between peaks was found to be higher on the serpentine micro-column compared to the spiral micro-column configurations except for the peak pairs 11-12, 12-13, and 14-15, when the circular micro-column configuration resulted in higher resolution. Among the spiral configurations the circular spiral configuration resulted in higher resolution between peaks compared to square spiral micro-columns.

In addition to the enhanced GC performance associated with using a serpentine channel configuration of the invention, another advantage associated with serpentine configuration is that more serpentine micro-columns may fit on a 4 inch wafer compared to the other spiral configurations, which translates into lower manufacturing costs for serpentine micro-columns. With respect to the two analytical microcolumn configurations shown in FIG. 1, the spiral micro-column (Panel A) and the serpentine micro-column (Panel B) channel configurations were fabricated on a silicon wafer. The spiral and serpentine micro-columns were about 3 meters long and about 100 microns wide, and were etched to a depth of about 100 microns using a deep reactive ion-etching (DRIE) process. The spiral channel structure had a lower dispersion for a Dean number below $\sqrt{2}/32=0.044$, where the dean number was calculated based on the radius of the inner-most bend of the spiral. The serpentine geometry gave lower dispersion when the Dean Number of the spiral was greater than $\sqrt{2}/16=0.088$. Table 3, immediately below, provides the Dean number for flow of hydrogen at 50 cm/sec in a 100 micron spiral micro-column with 100 micron spacing between channels.

TABLE 3

| Radius of curvature of inner bend, cm | Dean Number | Aspect ratio | Diameter of 1 meter long 100 micron diameter column cm with 100 microns between channels cm | Diameter of 3 meter long 100 micron diameter column cm with 100 microns between channels cm | Area of 1 meter long 100 micron diameter column cm with 100 microns between channels cm$^2$ | Area of 3 meter long 100 micron diameter column cm with 100 microns between channels cm$^2$ |
| --- | --- | --- | --- | --- | --- | --- |
| 0.01 | 0.471 | 1 | 1.60 | 2.76 | 2 | 6 |
| 0.05 | 0.211 | 5 | 1.60 | 2.77 | 2.01 | 6.01 |
| 0.10 | 0.149 | 10 | 1.61 | 2.77 | 2.03 | 6.03 |
| 0.284 | $\sqrt{2}/16$ | 28.4 | 1.69 | 2.82 | 2.25 | 6.25 |
| 0.30 | 0.086 | 30 | 1.70 | 2.83 | 2.28 | 6.28 |
| 0.50 | 0.067 | 50 | 1.88 | 2.94 | 2.79 | 6.79 |
| 0.75 | 0.054 | 75 | 2.19 | 3.14 | 3.77 | 7.77 |
| 1.00 | 0.047 | 100 | 2.56 | 3.41 | 5.14 | 9.14 |
| 1.136 | $\sqrt{2}/32$ | 11.4 | 2.78 | 3.58 | 6.06 | 10.06 |
| 2.00 | 0.033 | 200 | 4.31 | 4.86 | 14.57 | 18.57 |
| 3.00 | 0.027 | 300 | 6.21 | 6.61 | 30.27 | 34.27 |
| 4.00 | 0.024 | 400 | 8.16 | 8.46 | 52.27 | 56.27 |

The dean number was about $\sqrt{2}/16$ when the aspect ratio (the inner radius of the serpentine/the micro-column diameter) was at least about 28.4. The serpentine channel structure may be improved when the micro-column is less than about 2.78 cm across, for about a 1 meter micro-column and less than about 3.58 cm for a 3 m micro-column. About a 1 meter spiral micro-column would be required to have a diameter of about 2.78 cm to have the same dispersion as a serpentine micro-column. The serpentine micro-column would cover about 2 cm$^2$ of chip area (i.e., 1.cm×2 cm) while the spiral would cover about $\pi/4*2.78^2+2=6.06$ cm$^2$.

To put this in perspective, 18 serpentine micro-columns may fit on about a 4 inch wafer compared to only about 9 spiral micro-columns with a similar peak capacity. This translates into lower manufacturing cost for the serpentine micro-columns. Thus, contrary to the teachings in the known literature, serpentine micro-columns are surprisingly more effective than spiral ones for chip based GC. Table 4, immediately below, shows the number of 100 micron serpentine and spiral micro-columns that can fit onto a 4 inch wafer where the total micro-column length is about 1 meter, and the dean number for the spiral micro-column is about $\sqrt{2}/16=0.088$ at a hydrogen velocity of about 50 cm/sec and a pressure of about 1 atm so that the peak capacity of the two micro-columns would be similar. Notice that more serpentine micro-columns can be fabricated out of the 4 inch wafer provided that the ratio of the channel diameter to spacing between channels is less than about 4.

TABLE 4

| Space between channels microns | Ratio of channel diameter to spacing between channels | Number of serpentine columns that can fit onto a 4 inch wafer | Number of spiral columns that can fit onto a 4 inch wafer |
| --- | --- | --- | --- |
| 100 | 1 | 18 | 9 |
| 200 | 2 | 12 | 8 |
| 300 | 3 | 9 | 7 |
| 400 | 4 | 7 | 7 |
| 500 | 5 | 6 | 7 |
| 600 | 6 | 4 | 4 |
| 700 | 7 | 3 | 4 |

In general, the peak capacity increases as the micro-column diameter decreases. Diameters less than about 20 microns are not useful because the pressure drop in the micro-column increases without a corresponding increase in micro-column capacity or resolution. In Table 5, below, the peak capacity for specific micro-column diameters is shown. The peak capacities (peaks per second) were calculated from the Golay equation:

$$HETU = \frac{53 \frac{mm^2}{\sec}}{V} + 6.5 \times 10^{-3} \frac{\sec}{micron^2} V d^2 + 1.8 \times 10^{-7} \frac{\sec^2}{cm} V^2$$

With $V = 500$ mm/sec

TABLE 5

| Column Diameter Microns | Peak Capacity peaks/sec | Pressure drop per meter, psi |
| --- | --- | --- |
| 1000 | 5.7 | 0.016 |
| 700 | 8.1 | 0.034 |
| 500 | 11.3 | 0.066 |
| 250 | 21.3 | 0.265 |
| 100 | 39.8 | 1.66 |
| 50 | 49.7 | 6.71 |
| 25 | 53.6 | 28.5 |
| 15 | 54.5 | 86.2 |
| 10 | 54.8 | 205.7 |

Figure 11:
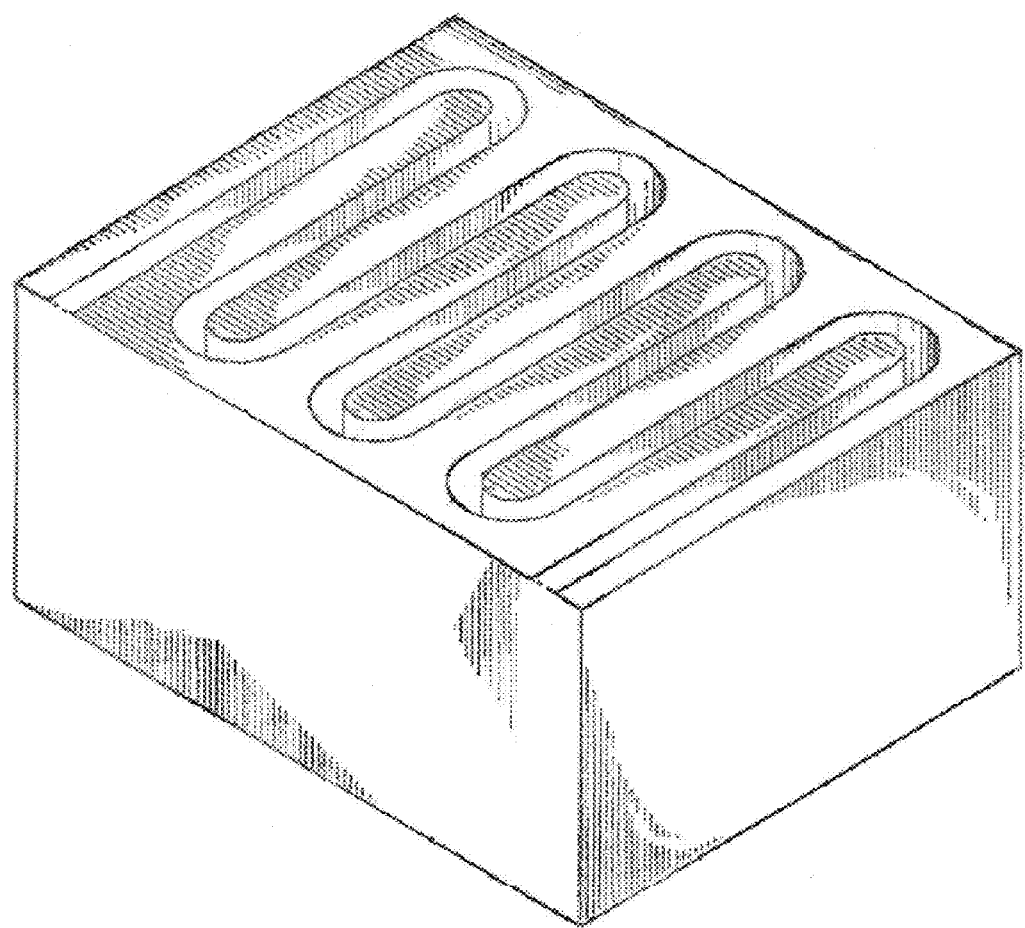
FIG. 11 is schematic showing a top view of an analytical micro-column having a serpentine channel structure constructed according to principles of the invention.

According to one embodiment, a top view of a serpentine channel structure is shown in FIG. 11. The micro-column channels may have a width in the range of about 20 microns to about 1000 microns, and specifically in a range of about 25 microns to 25.0 microns, and more specifically in the range of about 25 microns to about 50 microns. The micro-columns may have a depth in the range of about 20 microns to about 600 microns, and specifically between 50 and 250 microns. The micro-columns may have a length in the range of about 0.3 meters to about 50 meters, and in particular, a length of about 1 to 10 meters. The spacing between adjacent channels is less than about 4 times the micro-column channel diameter, and specifically may be in the range of about 30 microns to about 200 microns. In particular, in one particularly advantageous embodiment of the invention, the micro-columns may be about 3 meters long, about 100 microns wide, about 100 microns in depth, and have about 100 micron spacing between channels, for example.

Figure 12:
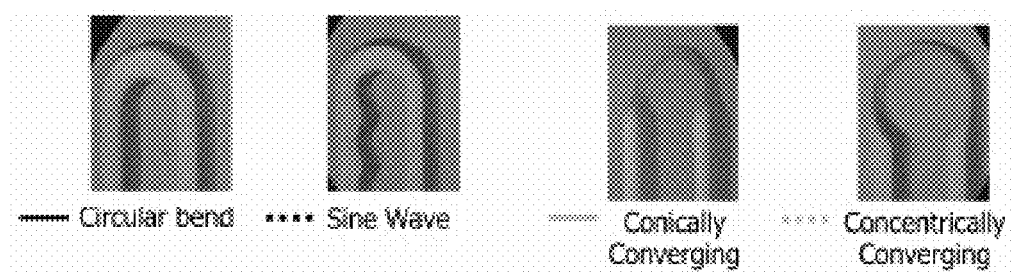
FIG. 12 is a graph showing the methane peaks observed on serpentine micro-columns with different turn geometries measured on about a 0.3 m long micro-column, according to principles of the invention. Panel A shows the difference turn geometries and Panel B shows the graph of the methane peaks.
Figure 12:
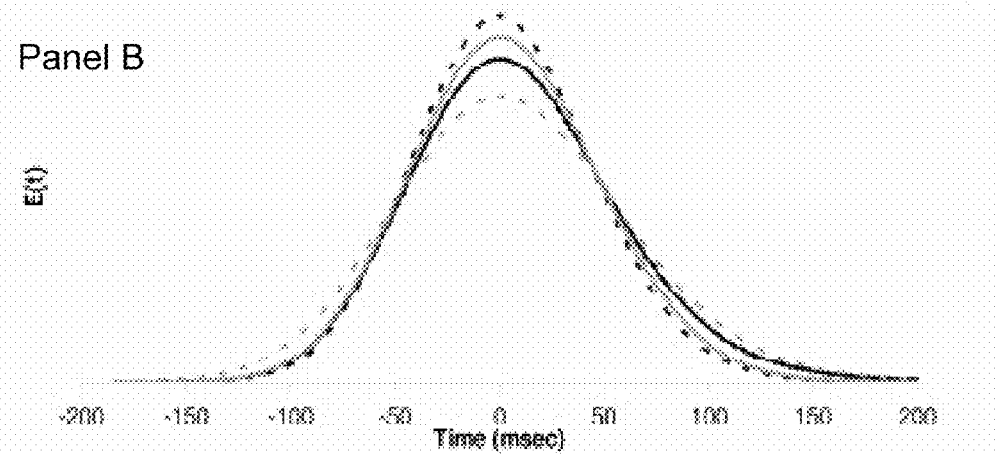

According to another embodiment of the invention, various turn geometries in the channel wall may be fabricated, which may produce improved μGC separation performance. Accordingly, three turn geometries (FIG. 12 (Panel A)) were tested with respect to the dispersion generated by a simple circular bend: (1) circular turn with a sine wave compensation structure, (2) a conically converging turn, and (3) a concentrically converging turn. The sine wave compensation structure was designed to reduce the strength of the Dean vortex using a series of expansions and contractions. The conically converging turns were adopted from the microcapillary electrophoresis literature to minimize dispersion due to race-track effect. The distortion in a band traveling about a turn was reduced if the width of the channel was reduced. Concentrically converging turn was an adaptation of the prior turn where the inner path bulges out to a certain radius to produce contraction at the turn. Comparison of the turn designs to the circular turn was performed using about a 30 cm long microchannel chip with about 22 pairs of turns fabricated on silicon. FIG. 12 (Panel B) shows methane pulses eluted from about 30 cm long serpentine micro-columns with different turn geometries. As shown in FIG. 12, Panel B, the sinusoidal compensation structured turn gave the lowest dispersion among the turn geometries tested.

According to particular aspects, the channels of the invention having specific turn geometries may be fabricated by etching the surface by deep reactive ion etching (DRIE), Bosch, or other etching processes appropriate for forming the desired channel structure in the material of the substrate or the wafer. Other suitable fabrication techniques may include mechanical machining or laser milling embossing or molding of polymeric compositions and, photo-lithography of UV-curable polymer compositions, and photoforming layers. Substrates or wafers that may be employed in the invention may be any solid material that can be formed into the preferred shape including in particular, metals, semiconductors, polymers, insulators, and glasses. Specific examples include silicon, germanium, zinc oxide, silicon carbide, pyrex, fused silica, quartz, thermal oxide, polyimide, PDMS, polyolefins, PET, PMMA, Polycarbonate, and Tri Acetyl Cellulose. Photoresists may include SU8 nickel, copper, tantalum, titanium, sapphire, and alumina.

According to one embodiment, the micro-columns of the invention may formed by placing a suitable cover on the top of the channels etched in the substrate, such as a glass cover or any other suitable material. Alternatively, the micro-column may be formed by placing a complementary etched wafer or substrate on top of second etched wafer such that the channels in each wafer are aligned.

The inside surfaces of the micro-columns may be coated with a stationary phase material to enhance the separation of the chemical analytes of interest in the gas mixture to be analyzed. The stationary phase material may be a polymer having a specific chemical group with the proper physico-chemical interaction to cause separation of the analytes. The micro-columns may be coated with the stationary phase material by a number of methods. Methods may include, for example, filling the micro-column with a solvent containing the stationary phase material and then applying a vacuum to the end of the micro-column to dry the solvent out of the micro-column, or by using sol-gel techniques. The stationary phase should be on the order of about 10-500 nm, uniformly spread over the micro-column's inner surface with minimum or no pooling.

The etching process used to fabricate the channels structures of the invention, however, may generate scallops, indentations, or rough edges in the walls of the channels. The rough edges are undesirable because they may interfere with attaining an uniform stationary phase deposition and ultimately effect the resolution of the GC by causing band broadening. Therefore, according to a further embodiments of the invention, the methodology may further include smoothening the channel walls by employing a buffered ion etching and/or an electrochemical etching process. Specifically, for example, the smoothening of DRIE channel walls in silicon by buffered oxide etching method includes growing an even 2 mm thick wet oxide followed by buffered oxide etch to remove wet oxide completely. The electrochemical etching route to smoothening DRIE channel walls in silicon involves growing porous silicon using electrochemical etching and etching porous silicon using mild potassium hydroxide (KOH). As an example, silicon electrochemical etching takes place at 0.25 A/cm$^2$ in a 1:1 hydrofluoric acid and ethanol electrolytic bath. Typical mild KOH concentrations include 5 to 10 molar solutions. The channel walls should be smoother than about one order of magnitude less than the phase thickness. For example, if the phase thickness is about 400 nm, then the channel walls should have a smoothness of about 40 nm or if the phase thickness is 100 nm, then the channel walls should have a smoothness of about 10 nm.

Figure 13:
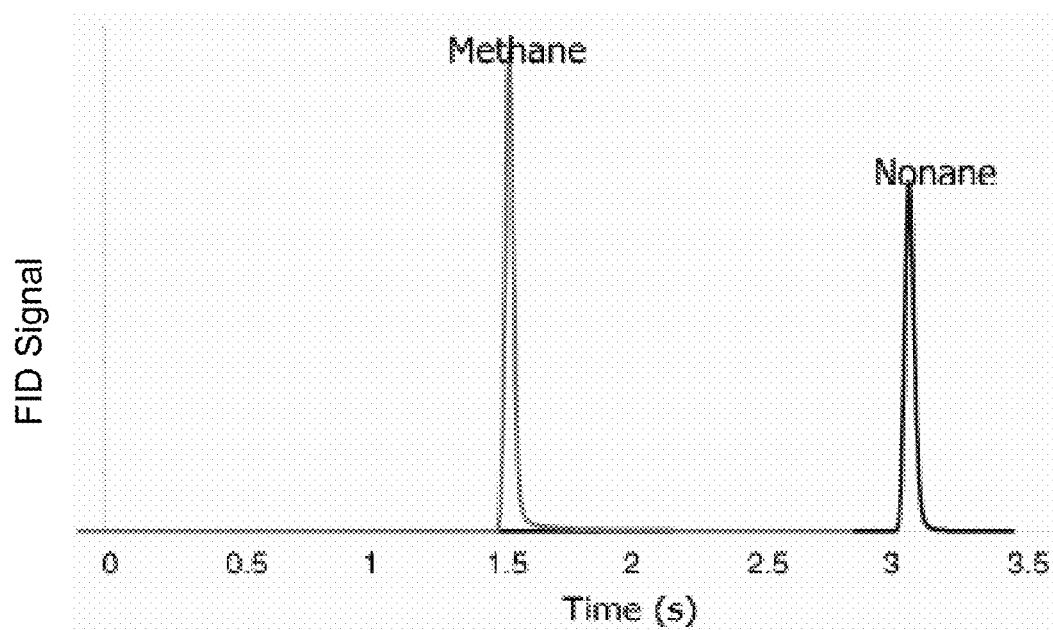
FIG. 13 is a plot showing the methane and nonane peaks seen in the 3 meter serpentine micro-columns constructed according to principles of the invention at high velocity.

FIG. 13 shows peaks measured on the serpentine micro-columns constructed according to smoothening principles of the invention. These micro-columns were 100 microns in diameter, 3 meters long with sinusoidal compensation structures and show peak capacities of about 90 in about 4 seconds using hydrogen as a carrier gas. This compares to a peak capacity of about 5 in about 4 seconds using air as a sweep gas. These results show that wall smoothing and device design have an important influence on micro-column performance.

Moreover, in addition to rough edges, the etching process may also create sharp bends in the channel structure, which may cause the stationary phase to build up in the corners of the bends and negatively effect the resolution of the GC. Therefore, if desired, the radius of the bend may be reduced by rounding off the bottom of the bend in the channel structure to promote uniform phase coating. The radius of the corner of the bend may be at least about 10 times larger than the phase thickness so with a 400 nm phase thickness, the corners should have a radius of more than 4 microns. The corners of the bends may be rounded off chemically using the electrochemical etching procedure described above, by machining or molding, or by coating with a suitable polymer or glass.

Figure 14:
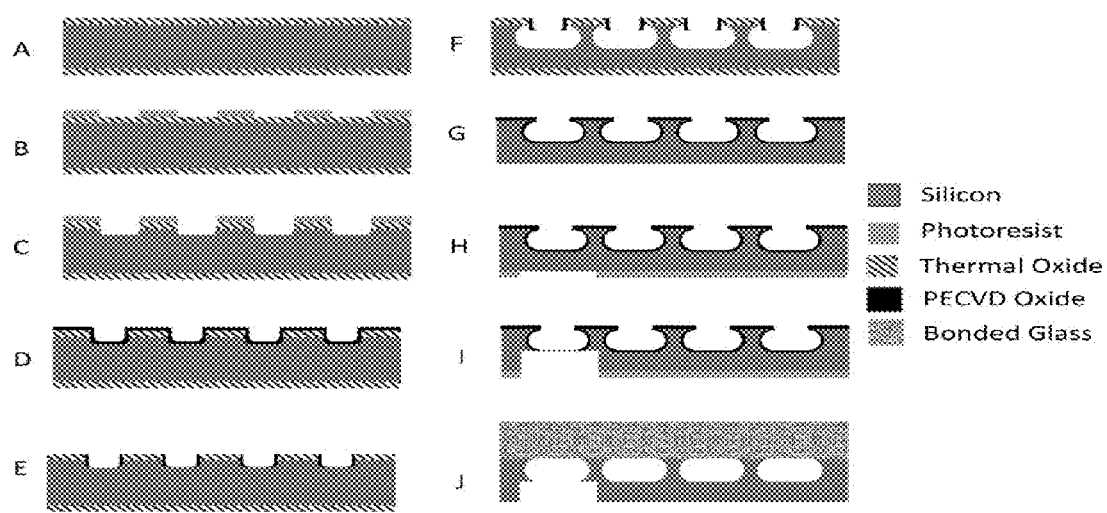
FIG. 14 provides a brief schematic outline of the fabrication process used to create partially buried micro-columns. The fabrication steps include 1.7 µm wet oxide growth (A), channel patterning using photolithography (B), CF4 RIE, DRIE, $SF_6$ RIE (C), photoresist strip, 0.3 µm PECVD oxide deposition (D), DRIE (E), $SF_6$ RIE (F), BOE etch, 1.7 µm wet oxide growth, BOE etch, 0.25 µm thick PECVD oxide deposition (G), access hole patterning using photolithography (H), DRIE of access holes (I), cleaning and anodic bonding (J). More detailed process information is provided in the text.

In one embodiment, a silicon micro-column with higher performance was fabricated by creating a rounded channel wall profile for a micro-column using the partially buried channel fabrication method, as follows, and schematically outlined in FIG. 14. The wafer processing steps includes micro-column fabrication (FIG. 14, steps A-G) followed by fabrication of fluidic access holes (FIG. 14, steps H-J). Microfabrication starts with a double side polished silicon wafer (4" diameter, 250 μm thick, 5-20 ohms-cm p-type, Silicon Quest International), which is first oxidized to grow a 1.7 μm thick wet oxide on the surface (FIG. 14A). Shipley SPR220-7 photoresist is spin coated on one side of the wafer at 3000 rpm. Photolithography is performed to obtain an image of 24 dies each containing 100 μm wide and 34 cm long serpentine channels (FIG. 14B). The patterned photoresist is baked at 90° C. for 30 minutes to withstand the subsequent reactive ion etching (RIE) steps. The channel pattern is transferred to the oxide layer using $CF_4$ RIE (also known as Freon RIE). Then exposed silicon surface in the channel region is etched 11 μm anisotropically using deep reactive ion etching (DRIE) (FIG. 14C). The DRIE is followed by a 4 min $SF_6$ isotropic RIE process to remove defects and produce cleaner micro-column structures. The photoresist is removed from the wafer using acetone before depositing 0.3 μm thick silicon dioxide ($SiO_2$) with plasma enhanced chemical vapor deposition (PECVD) (FIG. 14D). DRIE is performed for 20 minutes to etch the PECVD oxide deposited at the bottom of the channels. The latter step etches the PECVD oxide all over wafer except at the channel sidewalls (FIG. 14E). Isotropic etching of the wafer with $SF_6$ RIE for 25 minutes is used to create the partially buried channel structure (FIG. 14F). The wafer is then exposed to buffered oxide etch solution (BOE) to etch all the oxide. A wall smoothening step is introduced to reduce the channel wall roughness. The smoothening process involved growing 1.7 μm thick wet oxide followed by its etching with BOE. The channel side of the wafer is then protected from damage in the further processing steps by depositing a 0.25 μm thick PECVD oxide layer (FIG. 14G).

FIG. 15A shows a scanning electron microscope (SEM) image of the partially buried micro-column created by the fabrication process described above and in FIG. 14. The resultant channels were about 165 μm wide and about 65 μm deep. The hydraulic diameter of the channel was calculated to be about 107 μm. The SEM image shows that micro-column fabrication results in a partially buried isotropic wall profile. The capping of the partially buried channels with a flat Pyrex® lid would result in a cavity that looks like two channels with iso-etch wall profile align bonded together; the top channel having a single-etched wall profile and bottom channel having a single-etched wall profile with a rectangular ridge, similar to a double-etched iso-tropic profile. The walls were found to be smoother compared to the DRIE walls which are typically scalloped. The scallop-free walls minimize pooling of the stationary phase on the walls. No micro-grass, constrictions or fabrication defects were observed with the SEM in the channels inspected so far. FIG. 15B shows the 34 cm long micro-column die sizing 1.4 cm×1.4 cm, which was connected to the fused silica capillaries with Nanoports®.

Figure 15:
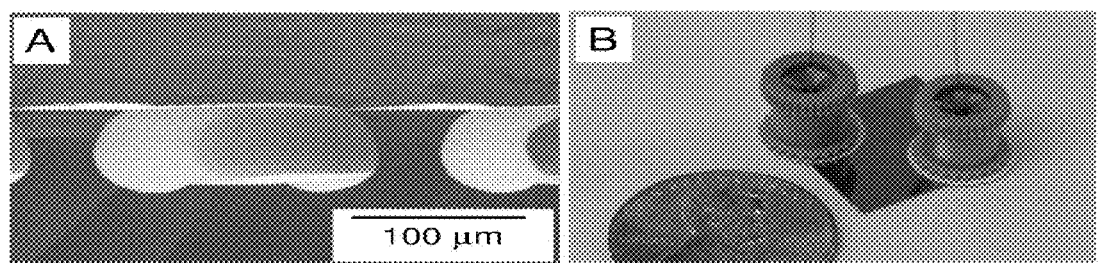
FIG. 15 are two photographs showing (A) SEM image showing the 165 μm wide and 65 μm deep cross-section of a partially buried micro-column of the invention; and (B) Photograph showing a 1.4 cm square micro-column die fabricated packaged with Nanoport® fittings connecting the access holes on the die to the fused silica capillaries.
Figure 16:
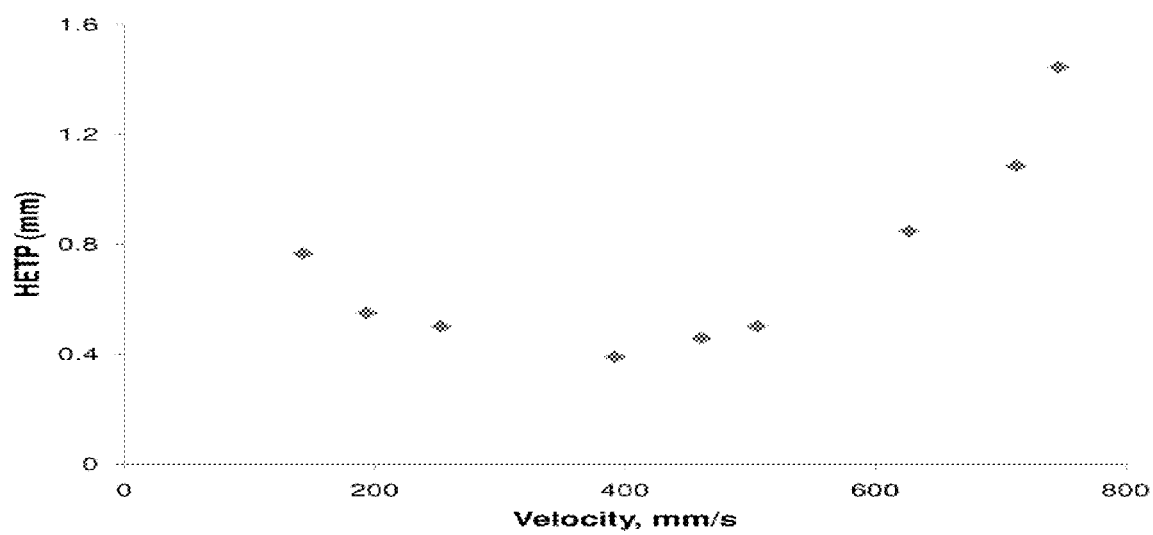
FIG. 16 shows a Golay plot for a 34 cm long, 165 μm wide×65 μm deep partially buried micro-columns of the invention generated using methane elution time for velocity measurements and n-$C_{10}$ elution time and peak width for HETP calculations. Temperature of the micro-column was adjusted to obtain a retention factor of 6.3 for n-$C_{10}$ at 25 cm/s of helium flow.

The performance of the buried micro-column of FIG. 15 was determined by taking micro-column efficient measurements. FIG. 16 shows the Golay plot obtained for the coated partially buried micro-column. The Golay plot shows a steep decrease in HETP value as the velocity increases to the optimum gas velocity and a steep increase in HETP value as the velocity increases beyond the optimal value. Minimum HETP was found to be 0.39 mm and the corresponding average velocity (optimum gas velocity) was found to be 40 cm/s.

Figure 17:
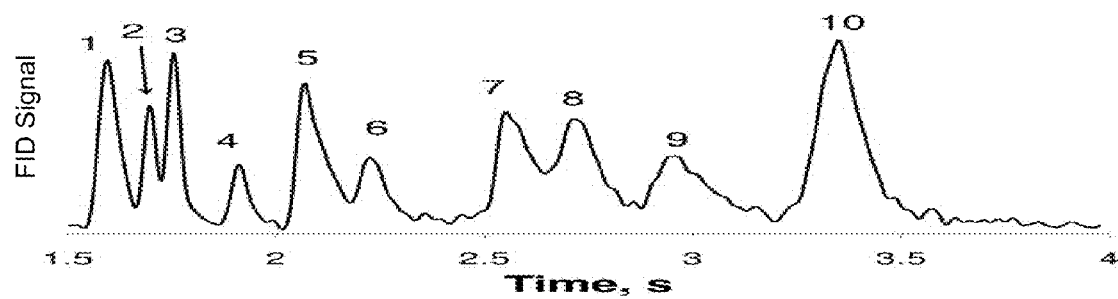
FIG. 17 is a plot showing separation of diethyl ether (1), toluene (2), n-$C_9$ (3), n-$C_{10}$ (4), dimethyl methyl phosphonate (5), n-$C_{11}$ (6), diethyl methyl phosphonate (7), diisopropyl methyl phosphonate (8), n-$C_{12}$ (9), and 1,6-dichlorohexane (10) mix obtained on a partially buried micro-column of the invention; 1 μl of headspace was injected with a 3000:1 split; injector temperature 250° C., inlet pressure of 13.5 psi, and oven temperature held at 85° C. Helium was used as the carrier gas.
Figure 18:
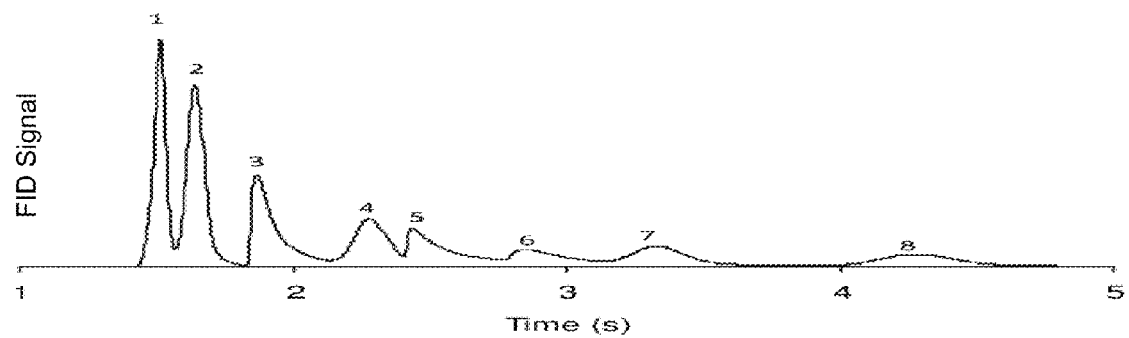
FIG. 18 is a chromatogram showing the separation of diethyl ether (1), toluene (2), dimethyl methyl phosphonate (3), diethyl methyl phosphonate (4), n-octanol (5), diisopropyl methyl phosphonate (6), 1,6-dichlorohexane (7), and dodecane (8) mix obtained on a DRIE silicon-Pyrex® micro-column; 1 μl of headspace was injected with a 100:1 split; injector temperature 250° C., inlet pressure of 25 psi, and oven temperature ramped from 90 to 98° C. at 120° C./min. Hydrogen was used as the carrier gas.

FIG. 17 shows the separation of a 10 compound mix on the coated partially buried micro-column of FIG. 15 within 3.6 s when the carrier gas inlet pressure and oven temperature were held at 13.5 psi and 85° C., respectively. The chromatogram shows a maximum peak width at half maximum of 0.2 s. The peaks elute in a different sequence on the partially buried micro-column compared to the one shown in FIG. 18 for the conventional DRIE micro-column. The alkanes were found to elute faster than the polar compounds. For example, on the partially buried micro-column n-$C_{12}$ elutes at 2.97 s compared to 1,6-dichlorohexane, which elutes at 3.36 s. However, on the DRIE micro-column 1,6-dichlorohexane elutes first at 2.86 s, while n-$C_{12}$ elutes at 4.29 s.

Figure 19:
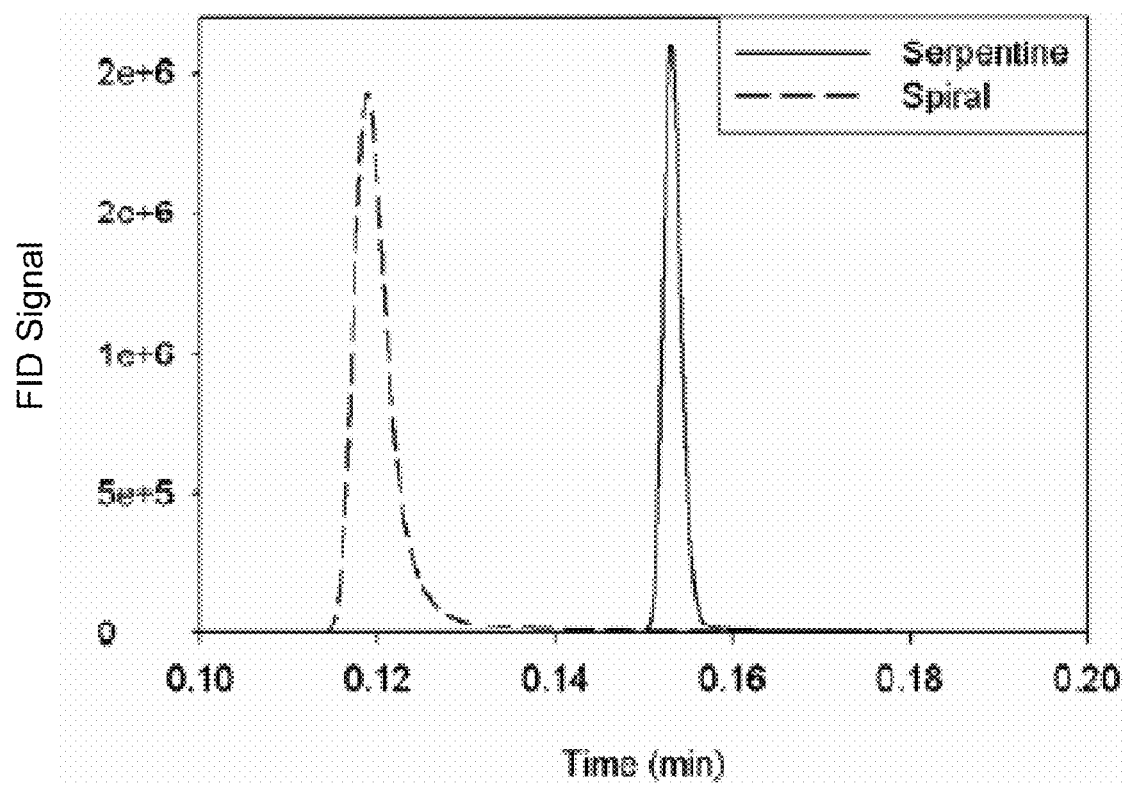
FIG. 19 is a graph comparing the methane peaks seen with a 3 meter long 100 micron wide and deep serpentine and spiral channels. The measurements were accomplished using about a 20 psi hydrogen sweep gas.
Figure 20:
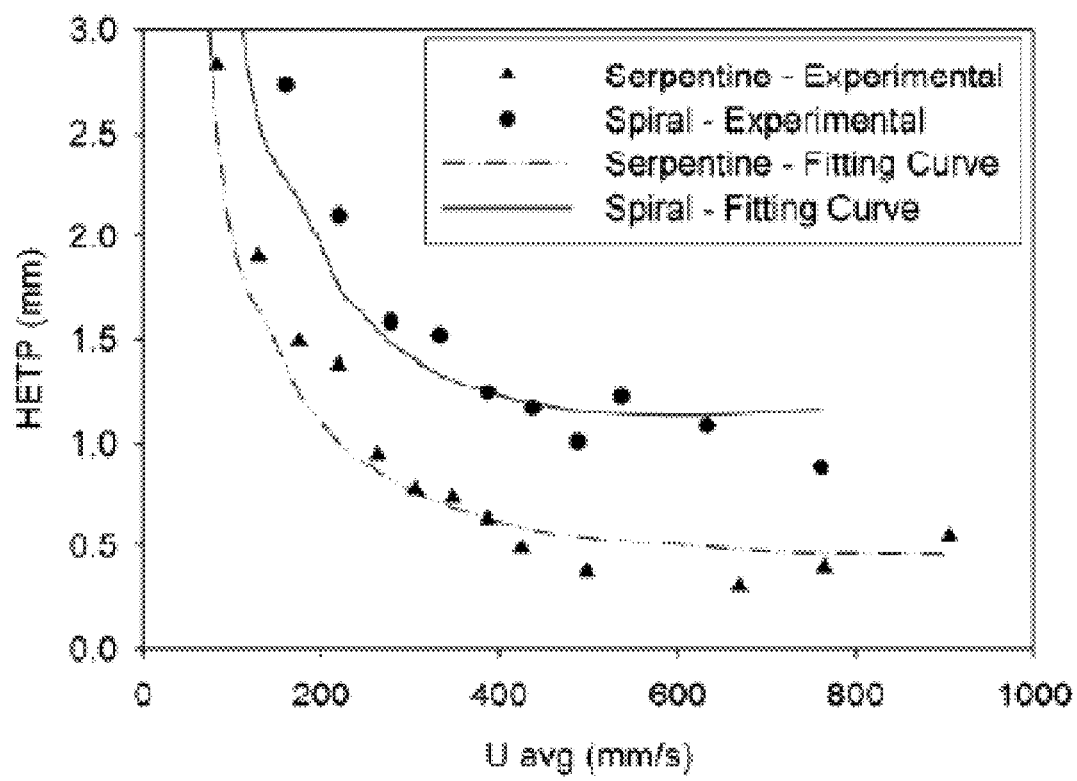
FIG. 20 are Golay plots comparing methane injections in 100 micron diameter, 3 meter long spiral micro-columns and serpentine micro-columns constructed according to principles of the invention.

FIG. 19 shows the elution profiles of a methane pulse from a serpentine micro-column that was constructed to the smoothening and rounding principles of the invention and a conventional spiral micro-column. The methane pulse eluting from a serpentine micro-column tailed less and exhibited about half the pulse width relative to the methane pulse eluting from the spiral micro-column. FIG. 20 shows the plot of calculated height equivalent to theoretical plates (HETP) versus average carrier gas velocity (u) to generate Golay plots of the methane injections. The Golay plots were theoretically modeled, shown as lines in FIG. 20, using the Golay-Guocheon kinetic model for where B is the coefficient for longitudinal diffusion, C is for resistance to mass transport in the gas phase and D is for extra micro-column band broadening. FIG. 20 shows that the serpentine micro-columns give lower HETP values compared to the spiral micro-columns.

Figure 21:
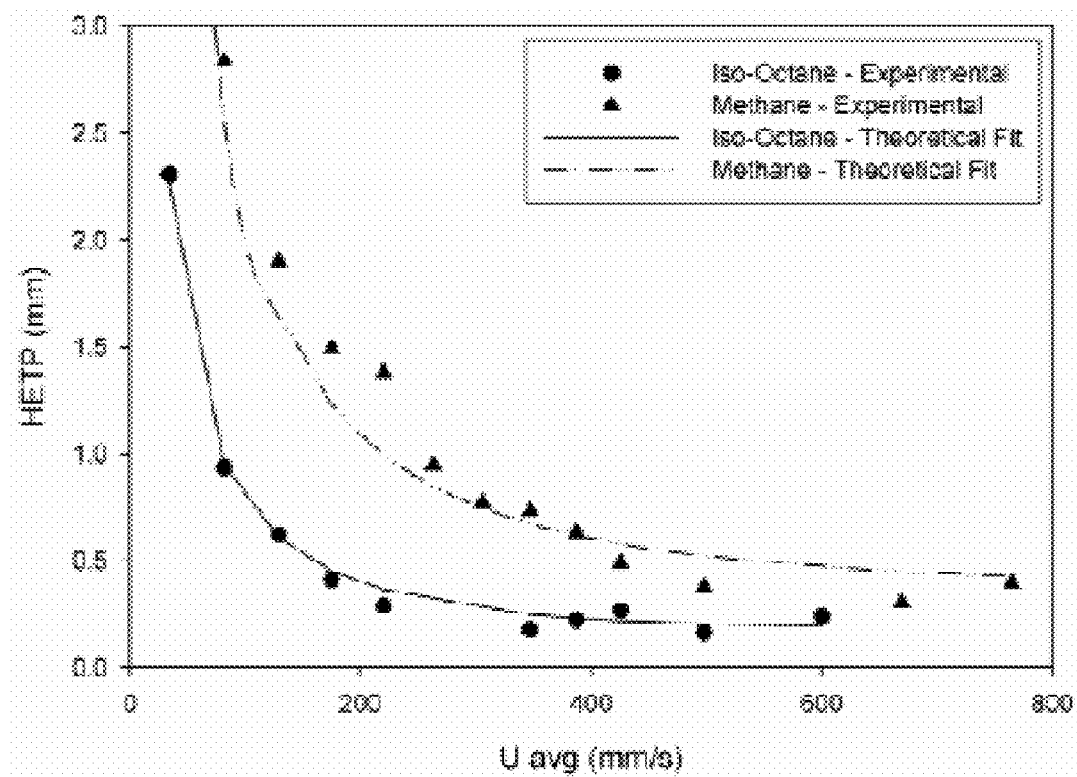
FIG. 21 are Golay plots comparing methane and isooctane separation in 100 micron diameter, 3 meter long serpentine micro-columns constructed according to principles of the invention.

FIG. 21 shows the difference between the Golay plots obtained using methane and isooctane as tracer molecule in efficiency calculations at same operating conditions for the serpentine micro-column of the invention. The HETP value decreased as the molecular weight increases, as expected from Taylor-Aris dispersion theory. See e.g., Bello, M. S.; Rezzonico, R.; Righetti, P. G., USE OF TAYLOR-ARIS DISPERSION FOR MEASUREMENT OF A SOLUTE DIFFUSION COEFFICIENT IN THIN CAPILLARIES. SCIENCE 1994, 266(5186), 773-776.

Without further elaboration, it is believed that one skilled in the art using the preceding description can utilize the invention to the fullest extent. The following examples are illustrative only, and not limiting of the disclosure in any way whatsoever.

EXAMPLES

Specific Example 1

Design and Fabrication of Micro-Columns

Microfabrication started with a double side polished silicon wafer (4" diameter, 250 μm thick, 5-20 ohms-cm p-type) from Silicon Quest International. The wafer was sputter coated with 1000 Å thick aluminum on one side. The aluminum layer protected the silicon surface from getting damaged during the fabrication steps prior to anodic bonding. Shipley SPR220-7 photoresist was spin-coated on both sides of the wafer at 3000 rpm. Double side lithography was performed to obtain an image of micro-channels on the aluminum side and fluid transfer holes on the silicon side. The chrome mask set for lithography was fabricated by Photo Sciences Inc. using a laser pattern generator. Micro-channel mask consisted of four 3.2 cm×3.2 cm dies each filled with 100 μm wide and 3 m long micro-channel folded in serpentine, circular-spiral, or square-spiral configuration. The serpentine micro-column design consisted of 25.9 mm long straight segments and turns of 100 μm inner diameter. The circular and square spiral designs consisted of two interlocked spiral channels connected by an S shaped segment (having 200 μm inner diameter turns) in the center of the chip. The second mask consisted of 210 μm wide fluid transfer holes for connecting the micro-channels from the bottom side. 10 micron wide crosses were designed in the masks to aid the alignment process. Exposed photoresist was developed in MIF327 developer. Overdevelopment with MIF327 was allowed to etch the underlying aluminum layer exposing the silicon surface for reactive ion etching. The patterned photoresist was baked at 140° C. for 30 minutes to withstand the plasma exposure in the reactive ion etching steps. Deep reactive ion etching was used to etch the channel patterns 100 μm deep and the access holes through the wafer. The micro-column dies were cleaned with Shipley Microposit Remover 1165 at 120° C. followed by an aluminum etching in type A aluminum etchant (Transene company), and a standard clean 1 (SC-1) at 73° C. Pyrex® 7740 glass pieces approximately of the size of micro-column die were cut out from wafers using an IR laser and cleaned using an SC-1 clean procedure. Silicon micro-columns were anodically sealed with the cleaned Pyrex® glass at 400° C. with 900 V bias. Two micro-columns of each configuration were fabricated for this example.

Specific Example 2

Passivation of Micro-Columns

Organosilicon hydride passivation using phenyltris(dimethylsiloxy)silane (Ah3P) (Gelest, SIP6826) was performed as disclosed in U.S. Appln. No. 61/021,620. The passivation was performed by dynamically coating the surface with a one micro-column length plug of neat reagent. A brass reservoir manifold containing the solution was attached on one of the micro-column access ports and the plug was pulled using a 660.4 mm Hg vacuum at the second access port. After the liquid plug exited the micro-column was heat-treated in a vacuum annealer (300 microns Hg) at a rate of 8° C. min$^{-1}$ to 375° C. and holding at the final temperature for 4 hours. The vacuum annealer was purged with nitrogen for 20 minutes before applying vacuum to ensure oxygen absence. The micro-column was cooled to room temperature before exposing to atmosphere.

Specific Example 3

Stationary Phase Coating

5% polar stationary phase, OV-5 vinyl gum obtained from Ohio Valley Specialty Company (Marietta, Ohio) was used as the stationary phase. The coating solutions were prepared in hexamethyldisilazane treated 12×32 vials obtained from Alltech (#72670). The stationary phase (in the range of 0.05-0.07 gm) was transferred to a vial using the closed end of a melting point capillary (Fisher Scientific, 12-141-5). 0.2 μm filtered pentane was injected into the capped vial using a 500 ml gas-tight syringe (Supelco, 509485) to produce a 4% (w/v) coating solution. The phase was dissolved by sonicating the vial for 20 minutes. Dicumyl peroxide (DCP) (Sigma Aldrich, >99%) in the form of freshly prepared 2% (w/v) toluene solution was added to the coating solution using a 10 μL syringe (Agilent Technologies, 5181-3354) to achieve a concentration of 0.2% (w/w) of the stationary phase.

The coating procedure was slightly modified from the methodology disclosed in U.S. Appln. No. 61/021,620. The ends of the micro-column were connected to a 3 m long fused silica capillary and a 1/16" PTFE tubing using Nanoports® (Upchurch Scientific, N-125S and N-333S respectively). During the coating process, Nanoports® were clamped physically and were not attached using the supplied preformed epoxy ring. 100 μm I.D. and 200 μm O.D. (Polymicro technologies, TSP100200) fused silica capillaries were used for connecting to the micro-column for coating purposes. The coating solution was introduced through the PTFE tubing using a clean 500 μl gas-tight syringe. Mild hand pressure was used to fill the coating solution into the micro-column and the post-column buffer capillary. The syringe was disconnected when four drops of coating solution left through post-column buffer capillary end. The Nanoport® (N-333S) with the PTFE tubing was unclamped and replaced by a Nanoport® (N-125S) connecting a 30 cm long pre-column buffer capillary. The latter was attached to a GC inlet and the coating solution was driven out using 0.8 psi helium pressure. When the coating solution exited the post-column buffer capillary, the solvent from the coated stationary phase was removed by passing helium at 40 psi inlet pressure for 10 minutes. Subsequently, the helium pressure was reduced to 0.8 psi and the stationary phase was cross-linked and conditioned by heating the micro-column to 160° C. overnight.

Specific Example 4

Post-Coating Treatment

Post-coating pinacolyl methylphosphonic acid (PMP) deactivation treatments were performed as disclosed in U.S. Appln. No. 61/021,620. The PMP treatment was performed on a conventional GC at 110° C. by injecting 1 μl of liquid PMP in the splitless mode (injector temperature of 250° C.) with a hydrogen flow at 40 psi followed by a stabilizing time of 1 hour with the hydrogen flowing. The micro-column was reconditioned at 200° C. with 40 psi inlet pressure for 4 hours. The completion of reconditioning process was checked with the presence of a stable FID baseline. The connecting fused silica capillaries were replaced with deactivated guard capillaries and Nanoports® were epoxied prior to testing separations in micro-columns.

Specific Example 5

Micro-Column Testing

An Agilent 6893N GC/FID-MS equipped with 7683B autosampler was used for all the separations. Packaged micro-columns were placed in the GC oven for testing and connected to the split inlet and FID using Restek deactivated guard capillaries (100 μm I.D., 200 μm O.D., and 25 cm long, IP deactivated). Hydrogen was used as carrier gas in all the tests. Test mixtures were prepared using puriss-grade chemicals (GC standards) from Aldrich (Milwaukee, Wis.).

Specific Example 6

Uncoated Micro-Column Tests

The packaged micro-columns were compared for their flow permeability by checking the average carrier gas velocity at different inlet pressures. The average carrier gas velocity was estimated using methane injections. Peak broadening in uncoated micro-columns of the three configurations was studied using two tracers, methane and isooctane. 1 μL of headspace vapor was injected with a split of 500:1 (injector temperature 250° C.); the micro-columns were held at 40° C. in the GC oven. The inlet pressure of the carrier gas was varied from 0.7 to 34 psi. The resulting chromatograms were analyzed using Peakfit software (v 4.12) to calculate the retention time, peak width at half maximum, and number of theoretical plates (N). N was used as a measure of comparison for dispersion in the different micro-column configurations. The number of theoretical plates was calculated by $$N = 5.54 \cdot \left(\frac{t_R'}{W_h}\right)^2 \quad (1)$$

where $t_R$ is the retention time, and $W_h$ is the full width at half maximum of the methane or iso-octane peak.

Specific Example 7

Coated Micro-Column Tests

The effect of micro-column configurations on temperature programmed separations was studied using an n-$C_7$ to n-$C_{13}$ mixture. The mixture was prepared by diluting 10 μL of equal weight mixture of n-alkanes (n-$C_7$ to n-$C_{13}$) in 1 ml of methylene chloride. 1 μL of the liquid mix was injected with a split of 500:1 (injector temperature 250° C.). The starting and final temperatures were 30° C. and 140° C. The effect of average carrier gas velocity was studied at nine values in the range of 5 cm/s to 65 cm/s keeping the temperature ramp rate at 10° C./min. The effect of temperature ramp rate was studied using three different ramp rates, 10° C./min, 25° C./min, and 40° C./min, keeping the average carrier gas velocity constant at 21 cm/s.

The concept of separation number (TZ, originally known as Trennzahl numbers) introduced by Kaiser was used to rigorously analyze the differences in separation capabilities of the micro-column configurations. The separation numbers were calculated by, $$TZ = \frac{t_{R(z+1)} - t_{Rz}}{w_{hz} + w_{h(z+1)}} - 1 \quad (2)$$

where z and z+1 refer to two consecutive members of the n-alkane paraffin homologous series, $t_R$ is the retention time, and $w_h$ is the full width at half maximum of the n-alkane peak. TZ values give the number of peaks which can be resolved between the two main peaks, having a 4.7σ-resolution between consecutive peaks. TZ was chosen as a measure because it is the only widely accepted term that can be applied to programmed-temperature analysis.

A 32 component multifunctional test mixture was also formulated to test the temperature programmed separation on micro-columns with different channel configurations. The components are listed in Table 6, below and are amongst commonly found air constituents or EPA listed air toxins.

TABLE 6

| | |
|---|---|
| 1 | Benzene |
| 2 | Heptane |
| 3 | 3-Pentanone |
| 4 | Toluene |
| 5 | Octane |
| 6 | 2-Hexanone |
| 7 | Chlorobenzene |
| 8 | Ethylbenzene |
| 9 | m-Xylene |
| 10 | Styrene |
| 11 | Nonane |
| 12 | 1,4-Dichlorobutane |
| 13 | α-Pinene |
| 14 | 1-Bromohexane |
| 15 | 3-Chlorotoluene |
| 16 | 1,3,5-Trimethylbenzene |
| 17 | 1,2,4-Trimethylbenzene |
| 18 | 1,3-Dichlorobenzene |
| 19 | Decane |
| 20 | Limonene |
| 21 | 1-Chlorooctane |
| 22 | Terpinolene |
| 23 | Undecane |
| 24 | 1,6-Dichlorohexane |
| 25 | 2-Ethoxyphenol |
| 26 | Naphthalene |
| 27 | 4-Decanone |
| 28 | Dodecane |
| 29 | 2-Decanone |
| 30 | 6-Undecanone |
| 31 | Tridecane |
| 32 | Carvacrol |

The mix was formulated by diluting 10 μL of equal weight mixture in 1 ml of methylene chloride. Chromatograms were produced by injecting 1 μL of the liquid mix with a split of 500:1 (injector temperature 250° C.). The starting and final temperature was set to 30° C. and 140° C., ramp rate of 10° C./min was used. Hydrogen was used as the carrier gas and the average carrier gas velocity was set to 40 cm/s. Resolution (Rs) of the peaks were calculated by, $$Rs = \frac{t_{R(z+1)} - t_{Rz}}{2(w_z + w_{(z+1)})} \quad (3)$$

where z and z+1 refer to two consecutive peaks used to calculate resolution, $t_R$ is the retention time, and w is the full widths at peak base. The chromatogram was processed in Peakfit software to calculate the peak resolutions.

Specific Example 8

Fabrication of Smoothened Walls

Figure 22:
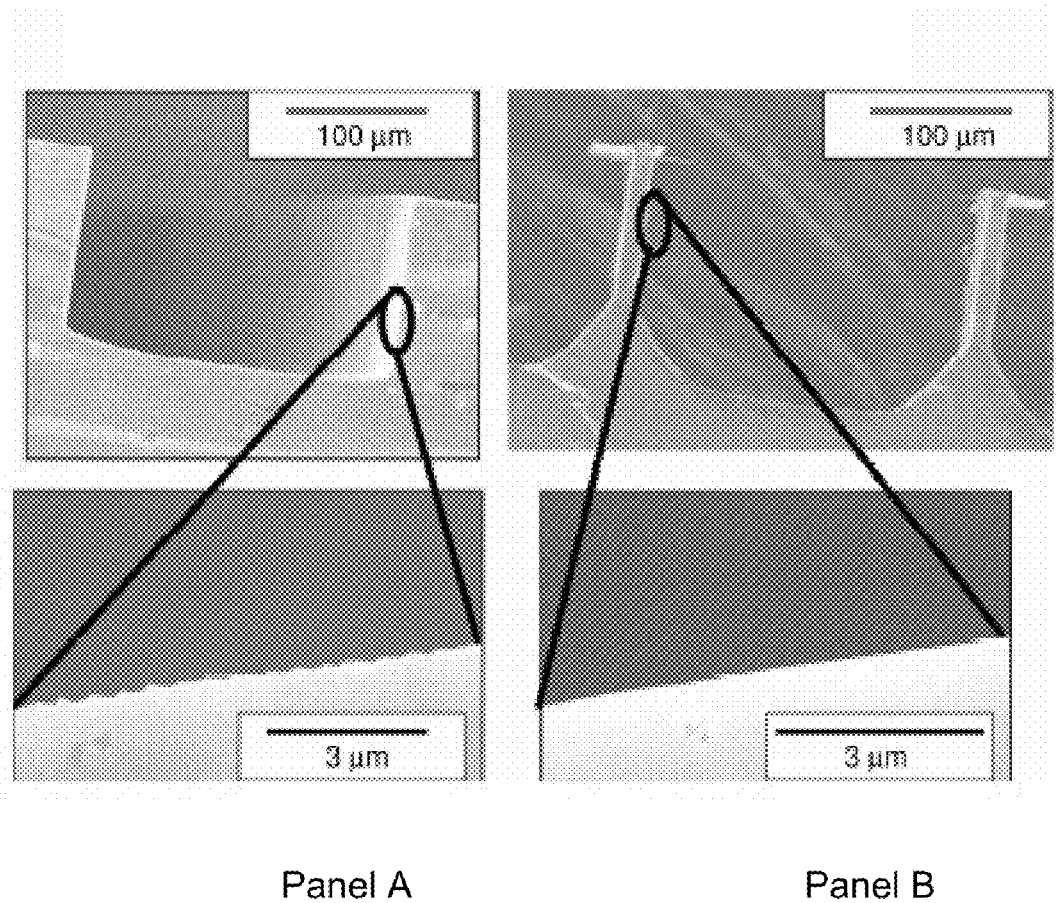
FIG. 22 is a micrograph showing the resultant shaping and smoothening of the micro-column walls obtained with electrochemical etching processes of the invention. Panel A shows the effects of shaping and smoothening of the micro-column walls using a conventional electrochemical etching process. Panel B shows the effects of shaping and smoothening of the micro-column walls using an electrochemical etching process according to principles of the invention.

The following fabrication sequence was employed to generate a 3 meter long micro-column with smoothened walls: (i) a (100) silicon wafer with 2 S 1813 was patterned for the channels and connection holes, (ii) oxide was patterned using $CF_4$ reactive ion-etching (RIE), (iii) PR was stripped and DRIE was performed on the micro-column side first to yield about 100 micron deep channels, (iv) DRIE was performed on the second side of the wafer to etch the access holes through the silicon wafer, simultaneously dicing the wafer, (v) smoothening the channel walls by either (a) growing 2 μm thick wet oxide followed by BOE etching, or (b) growing porous silicon using electrochemical etching followed by its removal with mild KOH, (vi) the/μGC micro-column dies were cleaned with BOE SC-1 and SC-2 sequentially, and (vii) the SC-1 cleaned Pyrex 7740 coverslips were anodically bonded to yield sealed micro-columns. FIG. 22 shows the resultant shaping and smoothening of the micro-column walls obtained with the electrochemical etching process.

The example given above is merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled chemical and/or mechanical engineering or in the relevant fields are intended to be within the scope of the appended claims.

The disclosures of all references and publications cited above are expressly incorporated by reference in their entireties to the same extent as if each were incorporated by reference individually.

What is claimed is:

1. A microfabricated gas chromatography column for separation of analytes in a gas mixture, said column comprising:
   a substrate having a top surface and a bottom surface;
   a plurality of adjacent channels in said substrate top surface, each channel having a generally serpentine configuration and including a plurality of bends, said bends having a configuration selected from the group consisting of a circular bend with a sine wave compensation, a conically converging turn, and a concentrically converging turn; and
   wherein the spacing between adjacent channels is less than about 4 times a diameter of said column.

2. The column of claim 1, wherein one of said channels diameter of a channel is in a range of about 20 microns to about 1000 microns.

3. The column of claim 1, wherein substrate is composed of one or more compounds selected from the group consisting of metals, polymers, glasses, ceramics including silicon, glass, polyimide, silicon carbide, PDMS, nickel, tantalum, titanium, and copper.

4. The column of claim 1, wherein a corner of at least one channel is rounded.

5. The column of claim 4, wherein both corners of each channel are rounded.

6. The column of claim 5, wherein the rounded corners merge to a form a contiguous arcuate profile.

7. The column of claim 1, wherein said channels are coated with a stationary phase compound having a thickness.

8. The column of claim 7, wherein a wall of said channel is smoothened to at least one tenth of the stationary phase thickness.

9. The column of claim 8, wherein the phase thickness is about 100 nm and the wall of said channel is smoothened to about 10 nm.

10. The column of claim 1, wherein a radius of a corner of the channel is rounded off to be at least 10 times larger than a thickness of a stationary phase coating said channels.

11. A microfabricated gas chromatography column for separation of analytes in a gas mixture, said column comprising:
   a substrate having a top surface and a bottom surface;
   a plurality of adjacent channels in said substrate top surface, each channel having a generally serpentine configuration and including a plurality of bends;
   wherein the spacing between adjacent channels is less than about 4 times a diameter of said column; and
   wherein said substrate consists of top and bottom wafers, each having a top and bottom surface, said plurality of adjacent channels being disposed in said top and bottom wafers such that when the wafers are adjacent to each other, channels from the top wafer are aligned with channels from the bottom wafer to define the column.

12. The column of claim 11, wherein the plurality of channels have rounded corners.

* * * * *